United States Patent
Levant et al.

(10) Patent No.: US 10,165,969 B2
(45) Date of Patent: Jan. 1, 2019

(54) POSITIONING A MEDICAL DEVICE BASED ON OXYGEN SATURATION MEASUREMENTS

(71) Applicant: LifeWatch Technologies, Ltd., Rehovot (IL)

(72) Inventors: Anna Levant, Rehovot (IL); Zohar Brachia Halevi, Ramat Gan (IL); Mordehay Amirim, Rehovot (IL)

(73) Assignee: BRAEMAR MANUFACTURING, LLC, Eagan, MN (US)

( * ) Notice: Subject to any disclaimer, the term of this patent is extended or adjusted under 35 U.S.C. 154(b) by 599 days.

(21) Appl. No.: 14/696,523

(22) Filed: Apr. 27, 2015

(65) Prior Publication Data

US 2016/0192868 A1    Jul. 7, 2016

Related U.S. Application Data

(63) Continuation-in-part of application No. 14/590,149, filed on Jan. 6, 2015.

(51) Int. Cl.
*A61B 5/1455* (2006.01)
*A61B 5/0402* (2006.01)
(Continued)

(52) U.S. Cl.
CPC ........ *A61B 5/14551* (2013.01); *A61B 5/0402* (2013.01); *A61B 5/04012* (2013.01);
(Continued)

(58) Field of Classification Search
CPC . A61B 5/021; A61B 5/02255; A61B 5/02407; A61B 5/02028; A61B 5/02055;
(Continued)

(56) References Cited

U.S. PATENT DOCUMENTS

| | | | | | |
|---|---|---|---|---|---|
| 5,273,036 | A | * | 12/1993 | Kronberg | A61B 5/02427 600/310 |
| 2008/0077026 | A1 | * | 3/2008 | Banet | A61B 5/02055 600/509 |
| 2010/0332173 | A1 | * | 12/2010 | Watson | A61B 5/02255 702/85 |
| 2011/0077486 | A1 | * | 3/2011 | Watson | A61B 5/021 600/324 |

(Continued)

*Primary Examiner* — Eric Winakur
*Assistant Examiner* — Chu Chuan (JJ) Liu

(57) ABSTRACT

A method that includes receiving first and second detection signals and electrocardiograph signals; wherein the first detection signals result from an illumination, by an oxygen saturation sensor included in a device that may be removably attached to a user, of a sternal angle of a user by infrared pulses; wherein the second detection signals result from an illumination, by the oxygen saturation sensor, of the sternal angle of a user by visible light pulses; wherein the electrocardiograph signals may be detected by an electrocardiography sensor that may be included in the device; generating a first waveform template that may be responsive to the first detection signals; generating a second waveform template that may be responsive to the second detection signals; calculating an indication of the oxygen saturation characteristic of the user in response to the first and second detection signals; detecting cardiac cycle durations that may be based upon the first and second detection signals; detecting electrocardiography based cardiac cycle durations; and evaluating a quality of the indication of the oxygen saturation characteristic of the user in response to the first waveform template, the second waveform template, the cardiac cycle's durations and the electrocardiography based cardiac cycle durations.

18 Claims, 21 Drawing Sheets

(51) Int. Cl.
*A61B 5/00* (2006.01)
*A61B 5/04* (2006.01)
*A61B 5/0452* (2006.01)

(52) U.S. Cl.
CPC ........ *A61B 5/04525* (2013.01); *A61B 5/6823* (2013.01); *A61B 5/7221* (2013.01); *A61B 5/721* (2013.01)

(58) Field of Classification Search
CPC . A61B 5/0402; A61B 5/1455; A61B 5/14551; A61B 5/14552; A61B 5/6823; A61B 5/72; A61B 5/0205; A61B 5/0059; A61B 5/04012; A61B 5/14553; A61B 5/7246
See application file for complete search history.

(56) References Cited

U.S. PATENT DOCUMENTS

| | | | |
|---|---|---|---|
| 2013/0060098 A1* | 3/2013 | Thomsen | A61B 5/02028 600/301 |
| 2013/0109937 A1* | 5/2013 | Banet | A61B 5/021 600/324 |
| 2013/0170609 A1* | 7/2013 | Nett | G06T 5/001 378/4 |
| 2013/0191035 A1* | 7/2013 | Chon | A61B 5/7207 702/19 |
| 2014/0073898 A1* | 3/2014 | Engelbrecht | A61B 5/7246 600/407 |
| 2015/0313484 A1* | 11/2015 | Burg | A61B 5/7257 600/301 |
| 2016/0151022 A1* | 6/2016 | Berlin | A61B 5/7246 600/301 |

* cited by examiner

500        FIG. 8

```
┌─────────────────────────────────────────────────────────────────────┐
│  ┌───────────────────────────────────────────────────────────────┐  │
│  │  Comparing the first cardiac cycle waveforms to the first     │  │
│  │  waveform template. 732                                        │  │
│  └───────────────────────────────────────────────────────────────┘  │
│                                                                      │
│  ┌───────────────────────────────────────────────────────────────┐  │
│  │  Calculating correlations between shapes of the at least some │  │
│  │  of the first cardiac cycle waveforms and a shape of the      │  │
│  │  first waveform template. 733                                  │  │
│  └───────────────────────────────────────────────────────────────┘  │
│                                                                      │
│  ┌───────────────────────────────────────────────────────────────┐  │
│  │  Converting at least some of the first cardiac cycle          │  │
│  │  waveforms to first duration-normalized and peak-normalized   │  │
│  │  cardiac cycle waveforms and calculating relationships        │  │
│  │  between shapes of the first duration-normalized and peak-    │  │
│  │  normalized cardiac cycle waveforms and a shape of the first  │  │
│  │  waveform template. 734                                        │  │
│  └───────────────────────────────────────────────────────────────┘  │
│                                                                      │
│  ┌───────────────────────────────────────────────────────────────┐  │
│  │  Calculating relationships between peaks of the at least some │  │
│  │  of the first cardiac cycle waveforms and a peak of the first │  │
│  │  waveform template. 735                                        │  │
│  └───────────────────────────────────────────────────────────────┘  │
│                                                                      │
│  ┌───────────────────────────────────────────────────────────────┐  │
│  │  Calculating relationships between durations of the at least  │  │
│  │  some of the first cardiac cycle waveforms and a duration of  │  │
│  │  the first waveform template. 736                              │  │
│  └───────────────────────────────────────────────────────────────┘  │
│                             731                                      │
└─────────────────────────────────────────────────────────────────────┘

┌─────────────────────────────────────────────────────────────────────┐
│  ┌───────────────────────────────────────────────────────────────┐  │
│  │  Comparing the second cardiac cycle waveforms to the second   │  │
│  │  waveform template. 732'                                       │  │
│  └───────────────────────────────────────────────────────────────┘  │
│                                                                      │
│  ┌───────────────────────────────────────────────────────────────┐  │
│  │  Calculating correlations between shapes of the at least some │  │
│  │  of the second cardiac cycle waveforms and a shape of the     │  │
│  │  second waveform template. 733'                                │  │
│  └───────────────────────────────────────────────────────────────┘  │
│                                                                      │
│  ┌───────────────────────────────────────────────────────────────┐  │
│  │  Converting at least some of the second cardiac cycle         │  │
│  │  waveforms to second duration-normalized and peak-normalized  │  │
│  │  cardiac cycle waveforms and calculating relationships        │  │
│  │  between shapes of the second duration-normalized and peak-   │  │
│  │  normalized cardiac cycle waveforms and a shape of the second │  │
│  │  waveform template. 734'                                       │  │
│  └───────────────────────────────────────────────────────────────┘  │
│                                                                      │
│  ┌───────────────────────────────────────────────────────────────┐  │
│  │  Calculating relationships between peaks of the at least some │  │
│  │  of the second cardiac cycle waveforms and a peak of the      │  │
│  │  second waveform template. 735'                                │  │
│  └───────────────────────────────────────────────────────────────┘  │
│                                                                      │
│  ┌───────────────────────────────────────────────────────────────┐  │
│  │  Calculating relationships between durations of the at least  │  │
│  │  some of the second cardiac cycle waveforms and a duration of │  │
│  │  the second waveform template. 736'                            │  │
│  └───────────────────────────────────────────────────────────────┘  │
│                             731'                                     │
└─────────────────────────────────────────────────────────────────────┘
```

FIG. 15

Receiving, by a computerized device, first and second detection signals and electrocardiography detection signals. The first detection signals result from an illumination, by an oxygen saturation sensor included in a device that is removably attached to a user, of a sternal angle of a user by infrared pulses. The second detection signals result from an illumination, by the oxygen saturation sensor, of the sternal angle of a user by visible light pulses. The electrocardiograph detection signals are generated by an electrocardiography sensor that is included in the device. 1010

Generating a first waveform template that is responsive to the first detection signals. 1020

Calculating an indication of the oxygen saturation characteristic of the user in response to the first and second detection signals. 1040

Detecting cardiac cycle durations that are based upon the first and second detection signals. 1050

Generating a second waveform template that is responsive to the second detection signals. 1030

Detecting electrocardiography based cardiac cycle durations. 1060

Evaluating a quality of the indication of the oxygen saturation characteristic of the user in response to the first waveform template, the second waveform template, the cardiac cycle's durations and the electrocardiography based cardiac cycle durations. 1070

POSITIONING A MEDICAL DEVICE BASED ON OXYGEN SATURATION MEASUREMENTS

RELATED APPLICATIONS

This application is a continuation in part of U.S. patent application Ser. No. 14/590,149 filing date Jan. 6, 2015 which is incorporated in reference.

BACKGROUND OF THE INVENTION

Oxygen saturation measurements provide highly valuable information about the state of a user. Results of oxygen saturation measurements depend upon the location of measurement and may be required to be taken over relatively long periods.

There is a growing need to provide methods for accurate oxygen saturation measurements that can be easily taken over long periods of time.

SUMMARY OF THE INVENTION

According to an embodiment of the invention there may be provided a method for measuring oxygen saturation of a user, the method may include: receiving, by a computerized device, first and second detection signals and electrocardiograph signals; wherein the first detection signals result from an illumination, by an oxygen saturation sensor included in a device that may be removably attached to a user, of a sternal angle of a user by infrared pulses; wherein the second detection signals result from an illumination, by the oxygen saturation sensor, of the sternal angle of a user by visible light pulses; wherein the electrocardiograph signals may be detected by an electrocardiography sensor that may be included in the device; generating a first waveform template that may be responsive to the first detection signals; generating a second waveform template that may be responsive to the second detection signals; calculating an indication of the oxygen saturation characteristic of the user in response to the first and second detection signals; detecting cardiac cycle durations that may be based upon the first and second detection signals; detecting electrocardiography based cardiac cycle durations; and evaluating a quality of the indication of the oxygen saturation characteristic of the user in response to the first waveform template, the second waveform template, the cardiac cycle's durations and the electrocardiography based cardiac cycle durations.

The method may include applying a high-pass filter and a bilateral filter on the first detection signals to provide first filtered detection signals.

The generating of the first waveform template may include filtering the first detection signals to provide first filtered detection signals; and detecting first cardiac cycle waveforms in the first filtered detection signals.

The detecting of the cardiac cycle durations may include measuring durations of the first cardiac cycle waveforms.

The generating of the first waveform template may include converting the first cardiac cycle waveforms to first duration-normalized cardiac cycle waveforms that have a same duration.

The generating of the first waveform template may be responsive to at least some of the first duration-normalized cardiac cycle waveforms.

The generating of the first waveform template equals an average of at least some of the first duration-normalized cardiac cycle waveforms.

The generating of the first waveform template further may include calculating, for each first duration-normalized cardiac cycle waveform, a similarity score indicative of a similarity between the first duration-normalized cardiac cycle waveform and other first duration-normalized cardiac cycle waveforms.

The generating of the first waveform template further may include ignoring at least one first duration-normalized cardiac cycle waveform based upon similarity scores of the first duration-normalized cardiac cycle waveforms.

The calculating, for each first duration-normalized cardiac cycle waveform, of the similarity score may include calculating a plurality of Pearson correlation coefficients between the first duration-normalized cardiac cycle waveform and a plurality of other first duration-normalized cardiac cycle waveforms.

The calculating, for each first duration-normalized cardiac cycle waveform, of the similarity score may include summing the plurality of Pearson correlation coefficients.

The method may include calculating qualities of at least some of the first cardiac cycle waveforms; and wherein the quality of the first and second detection signals may be responsive to the qualities of the at least some of the first cardiac cycle waveform.

The calculating of the qualities of at least some of the first cardiac cycle waveforms may include comparing the at least some of the first cardiac cycle waveforms to the first waveform template.

The calculating of the qualities of at least some of the first cardiac cycle waveforms may include calculating correlations between shapes of the at least some of the first cardiac cycle waveforms and a shape of the first waveform template.

The calculating of the qualities of at least some of the first cardiac cycle waveforms may include converting at least some of the first cardiac cycle waveforms to first duration-normalized and peak-normalized cardiac cycle waveforms and calculating relationships between shapes of the first duration-normalized and peak-normalized cardiac cycle waveforms and a shape of the first waveform template; and wherein the first duration-normalized and peak-normalized cardiac cycle waveforms may be a same duration and a same peak value as the first waveform template.

The calculating of the qualities of at least some of the first cardiac cycle waveforms may include calculating relationships between peaks of the at least some of the first cardiac cycle waveforms and a peak of the first waveform template.

The calculating of the qualities of at least some of the first cardiac cycle waveforms may include calculating relationships between durations of the at least some of the first cardiac cycle waveforms and durations of corresponding electrocardiography based cardiac cycle durations.

According to an embodiment of the invention there may be provided a non-transitory computer readable medium that stores instructions that once executed by a computerized device cause the computerized device to execute the steps of: receiving first and second detection signals and electrocardiograph signals; wherein the first detection signals result from an illumination, by an oxygen saturation sensor included in a device that may be removably attached to a user, of a sternal angle of a user by infrared pulses; wherein the second detection signals result from an illumination, by the oxygen saturation sensor, of the sternal angle of a user by visible light pulses; wherein the electrocardiograph signals may be detected by an electrocardiography sensor that may be included in the device; generating a first waveform template that may be responsive to the first detection signals; generating a second waveform template that may be responsive to the second detection signals; calculating an indication of the oxygen saturation characteristic of the user in response to the first and second detection signals; detecting cardiac cycle durations that may be based upon the first and second detection signals; detecting electrocardiography based cardiac cycle durations; and evaluating a quality of the indication of the oxygen saturation characteristic of the user in response to the first waveform template, the second waveform template, the cardiac cycle's durations and the electrocardiography based cardiac cycle durations.

According to an embodiment of the invention there may be provided a medical device that includes a processor that includes one or more hardware components. The processor may be configured to (i) receive first and second detection signals and electrocardiograph signals; wherein the first detection signals result from an illumination, by an oxygen saturation sensor included in a device that may be removably attached to a user, of a sternal angle of a user by infrared pulses; wherein the second detection signals result from an illumination, by the oxygen saturation sensor, of the sternal angle of a user by visible light pulses; wherein the electrocardiograph signals may be detected by an electrocardiography sensor that may be included in the device; (ii) generate a first waveform template that may be responsive to the first detection signals; (iii) generate a second waveform template that may be responsive to the second detection signals; (iv) calculate an indication of the oxygen saturation characteristic of the user in response to the first and second detection signals; (v) detect cardiac cycle durations that may be based upon the first and second detection signals; (vi) detect electrocardiography based cardiac cycle durations; and (vii) evaluate a quality of the indication of the oxygen saturation characteristic of the user in response to the first waveform template, the second waveform template, the cardiac cycle's durations and the electrocardiography based cardiac cycle durations.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof may best be understood by reference to the following detailed description when read with the accompanying drawings in which:

FIGS. 13-15 illustrate a stage of processing the first and second detection signals to evaluate a quality of the first and second detection signals according to an embodiment of the invention;

FIG. 18 illustrates a method according to an embodiment of the invention;

Figure 1:
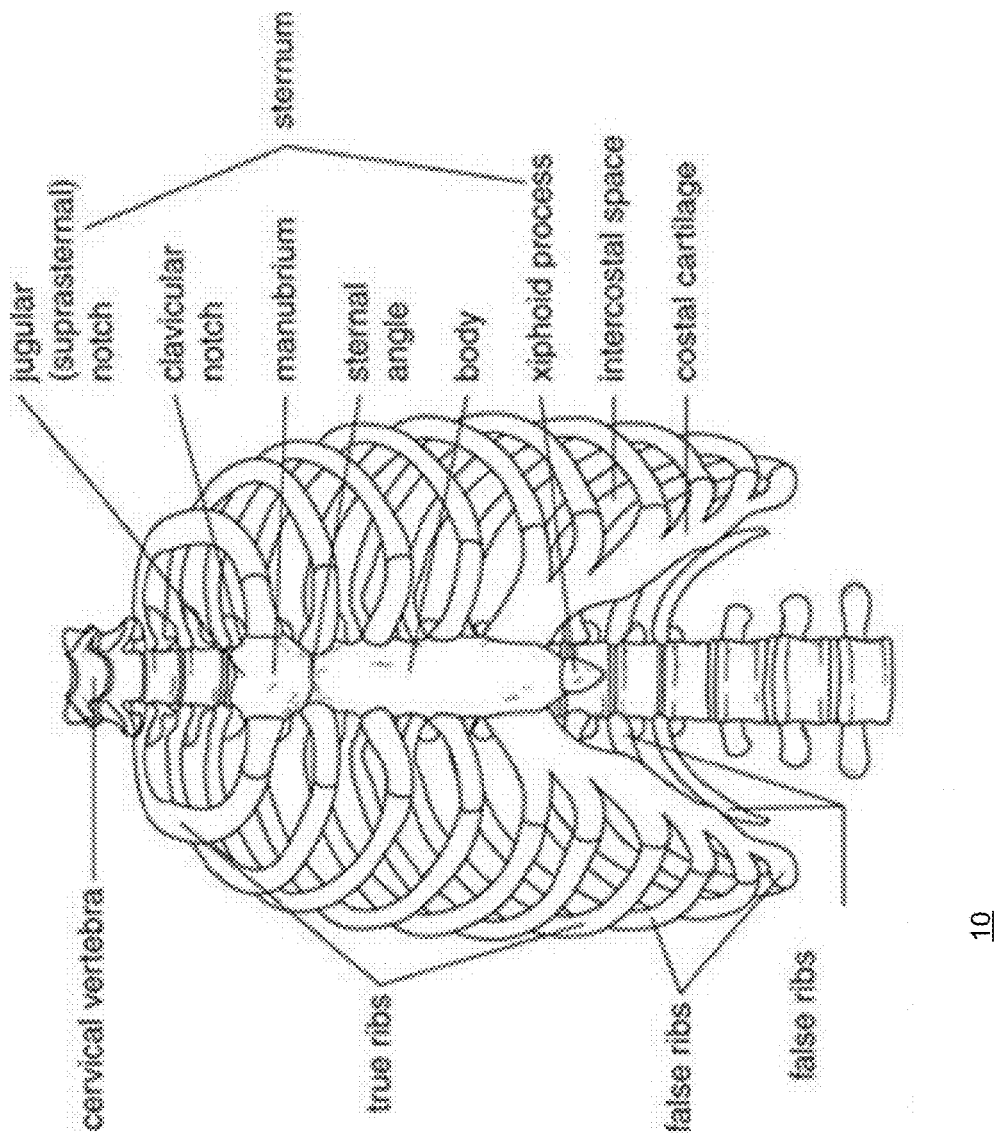
FIG. 1 illustrates the sternum and the ribs of a person.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

It has been surprisingly found that measuring oxygen saturation by illuminating the sternal angle of a user provides reliable results. The sternal angle is easy to find by the user (or third parties) so that users can easily and accurately position the sensor to face sternal angle. This greatly increases the repetitiveness of the oxygen saturation results. Furthermore—placing the device in this position reduces the breath induced movements that the device experiences and further increases the accuracy of this measurement. In addition—placing the device at that position is relatively easy as the sternum is relatively flat.

FIG. 1 illustrates the sternum and the ribs of a person 10. The sternum angle is located between the manubrium bone and the body of the sternum.

Figure 2:
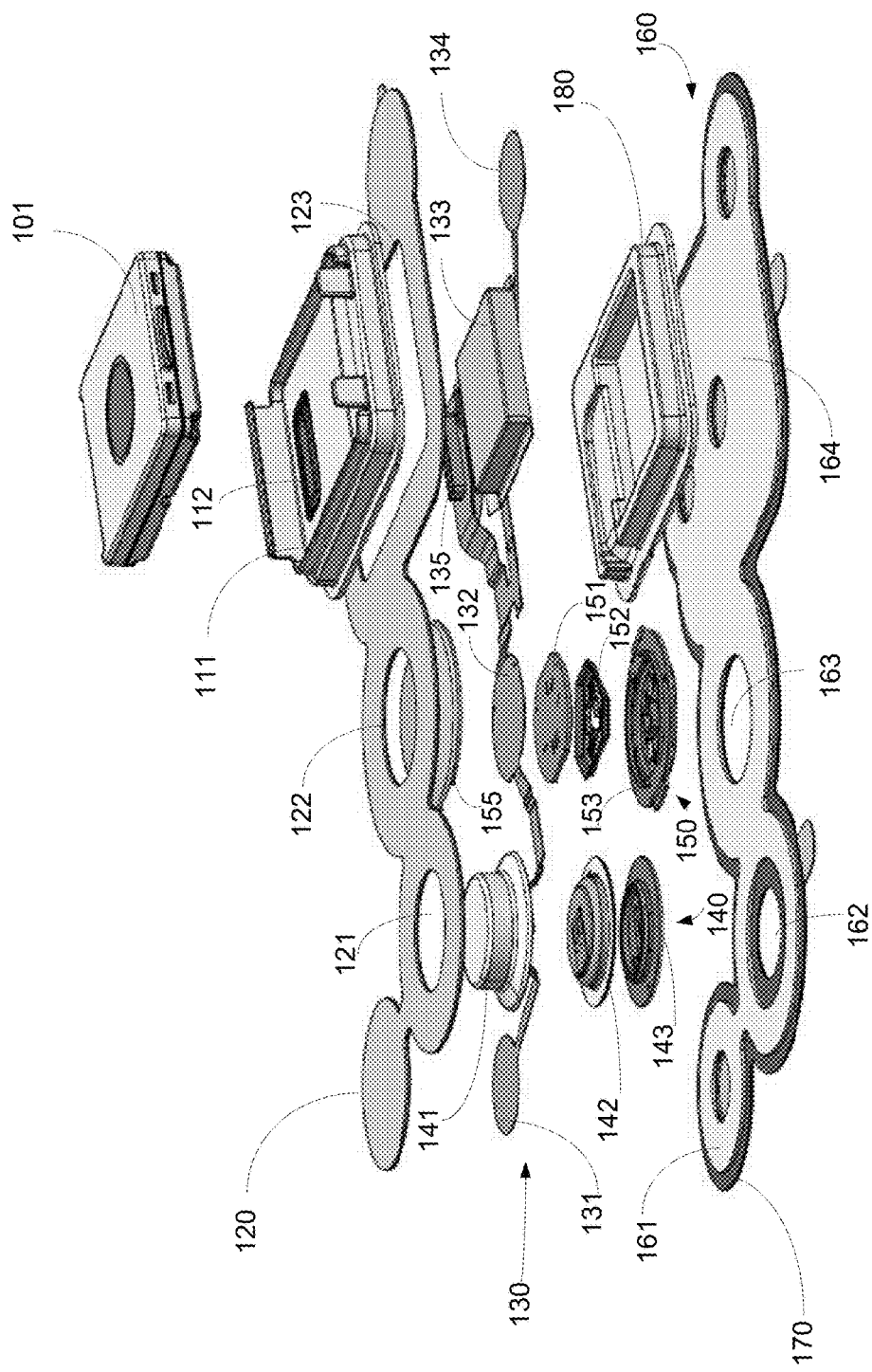
FIG. 2 is an exploded view of a device according to an embodiment of the invention.

FIG. 2 is an exploded view of a device 100 according to an embodiment of the invention.

Device 100 includes:
1. Processor and transceiver (collectively denoted 101).
2. An upper elastic layer 120 that include first, second and third openings 121, 122 and 123.
3. Intermediate layer 130 that includes conductors 131, 132 and 134 and socket 135 for conveying power from battery 133.
4. Temperature sensor 140 that includes temperature sensor cover 141, temperature sensor electrical board 142 and temperature sensor case 143.
5. Oxygen saturation sensor 150 that includes oxygen saturation sensor electrical board 151, 151, oxygen saturation sensor shield 152 and oxygen saturation sensor case 153.
6. A lower elastic layer 160 that include first, second and third openings 161, 162 and 163 and an addition portion 164 to be contacted by lower case 180. The lower elastic layer 160 has an underside provided with a self-adhesive. Removable cover 170 shields the self-adhesive and is removed before attaching the device 100 to a user.
7. Upper case 111 having socket 112.
8. Lower case 180.

The temperature sensor cover 141 is shaped and positioned to pass through the first opening 121 of the upper elastic layer 120. Cover 155 is arranged to seal the second opening 122 of the upper elastic layer 120. Cover 155 is positioned between the upper elastic layer 120 and conductor 132 of the intermediate layer 130. Conductor 132 is positioned above the oxygen saturation sensor electrical board 151.

The temperature sensor case 143 is positioned directly above the first opening 162 of the lower elastic layer 160.

The oxygen saturation sensor 150 is positioned directly above the second opening 163 of the lower elastic layer 160. It may contact the sternum angle during measurements but may be positioned slightly (few millimeters) above the sternum angle without contacting the sternum angle.

Battery 133 is placed within lower case 180 and its upper facet supports a lower facet of upper case 111 that is connected to the processor and transceiver 101.

Device 100 is illustrated as including a temperature sensor 140 and oxygen saturation sensor 150. It is noted that other sensor (or sensors) can be provided instead (or in addition) to the temperature sensor 140. Alternatively, the only sensor included in device 100 may be the oxygen saturation sensor 150. For an example (illustrated in FIG. 6), the device 100 may include a movement sensor 144, a temperature sensor 140 and the oxygen saturation sensor 150.

The device 100 may be very compact and light weight. Its transceiver (denoted 101(2) in FIG. 6) may be arranged to perform short range and/or long range transmissions.

Figure 3:
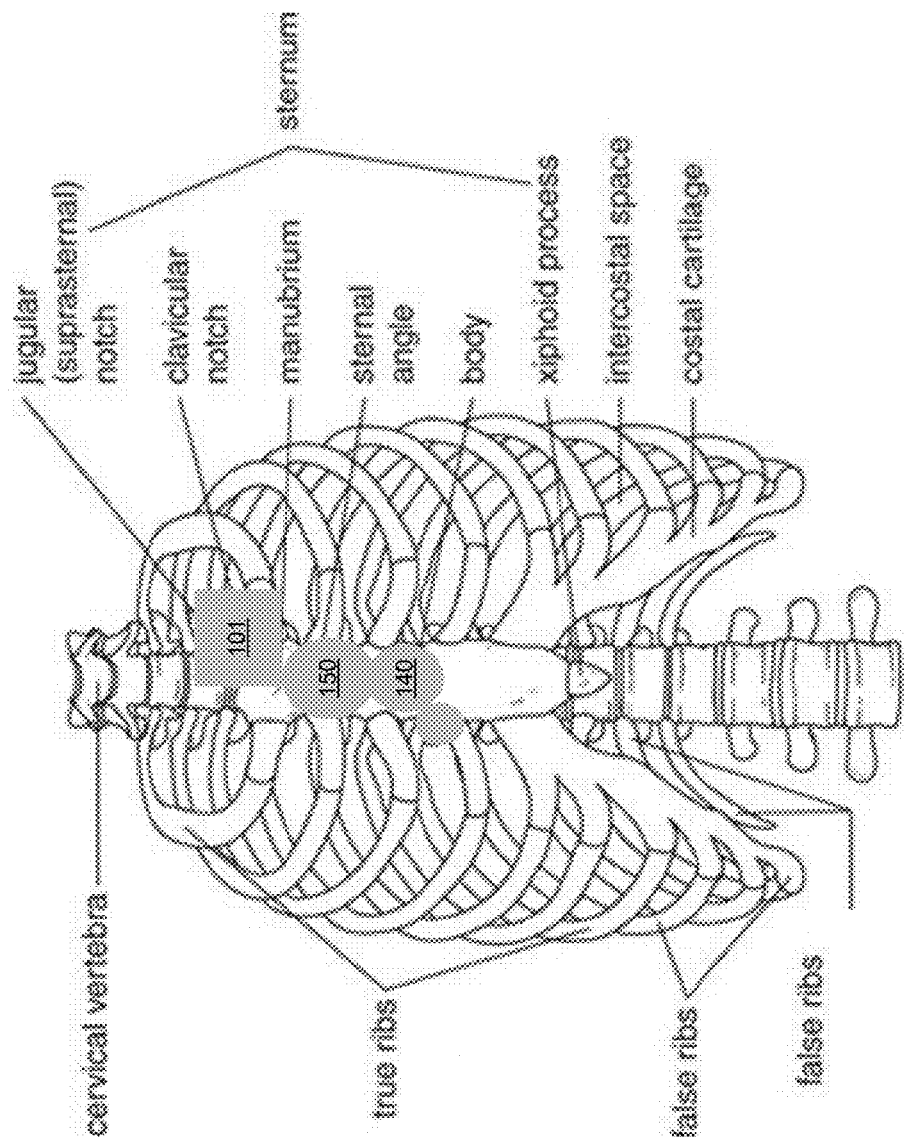
FIG. 3 illustrates a placement of the device of FIG. 2 on a chest of a user according to an embodiment of the invention.

FIG. 3 illustrates device 100 as being positioned on a user wherein the oxygen saturation sensor 150 is positioned directly above the sternum angle, the temperature sensor 140 is positioned below the sternum angle and the processor and transceiver 101 is positioned above the sternum angle.

Figure 4:
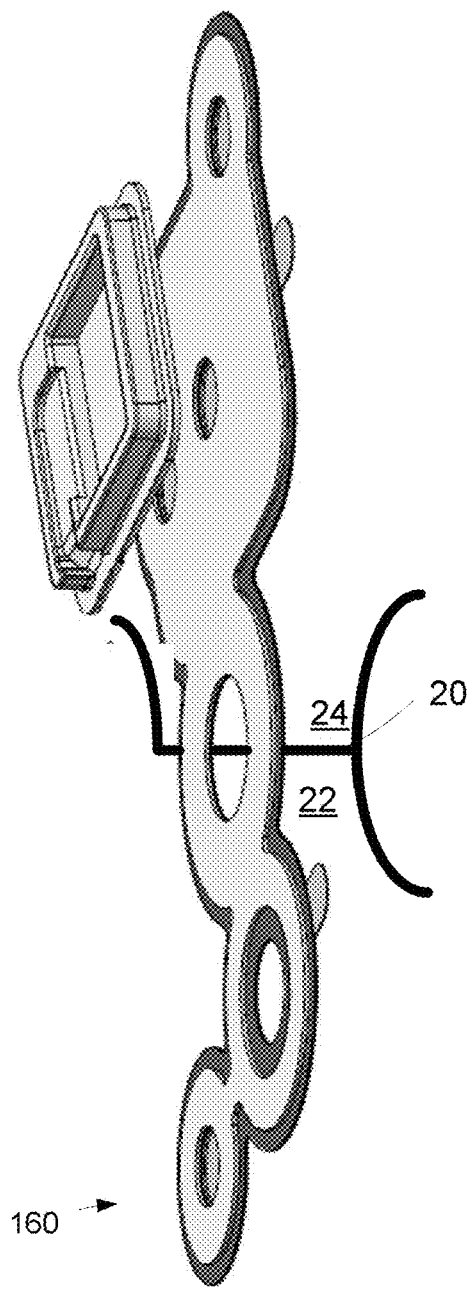
FIG. 4 illustrates a placement of the device of FIG. 2 on a chest of a user according to an embodiment of the invention.

FIG. 4 illustrates the lower elastic layer 160 of device 100 as being positioned on a user wherein the third opening 163 (that the oxygen saturation sensor 150 is positioned directly above) is positioned directly above the sternum angle 22, the temperature sensor 140 is positioned directly above the body 24 of the sternum and the lower case 180 faces the manubrium bone.

Figure 5:
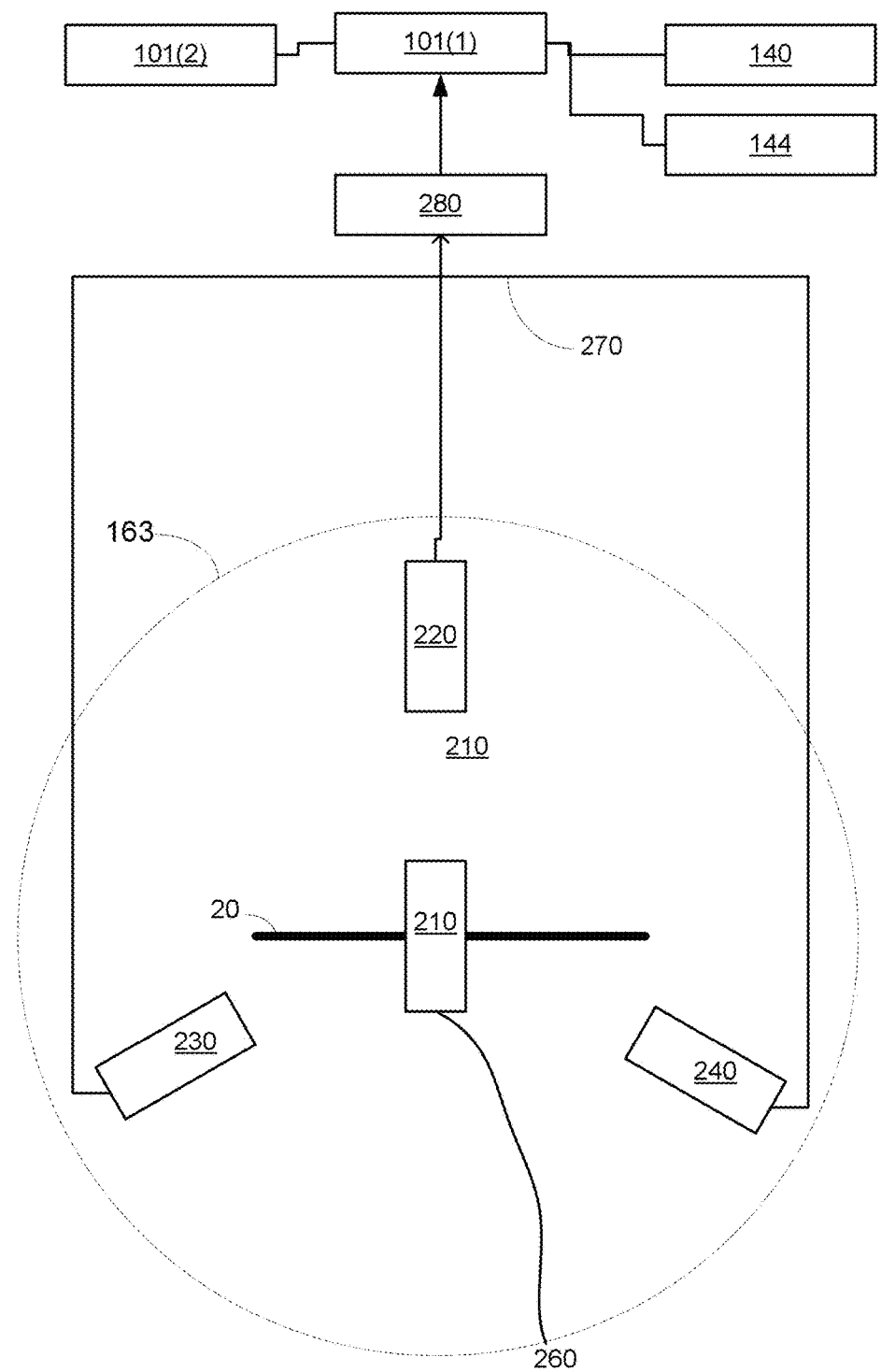
FIG. 5 is a schematic diagram of various components of the device of FIG. 2 according to an embodiment of the invention.

FIG. 5 is a schematic diagram of various components of the device 100 of FIG. 2 according to an embodiment of the invention.

FIG. 5 illustrates the oxygen saturation sensor 150 as including three radiation sensing elements 220, 230 and 240, illumination module 210 (illustrated as being positioned directly above the sternum angle 20 and within third opening 163 of the lower elastic layer 160), intermediate module 260 (that may include an analog amplifier, an analog to digital converter or a combination of both), processor 101(1) of processor/transducer 101, transducer 101(2), temperature sensor 140 and movement sensor 144.

The illumination module 210 may be arranged to illuminate the sternum angle with infrared pulses and visible light pulses. The radiation sensing elements 220, 230 and 240 may sense radiation reflected and/or scattered from the sternum angle in the infrared and visible light ranges and send detection signals towards intermediate module 260.

Pulses of energy are provided to the illumination module 210 via conductor 270.

Radiation sensing elements 220, 230 and 240 are coupled in parallel to each other via conductor 270 but may be coupled in a serial manner to each other.

Processor 101(1) may receive detection signals from temperature sensor 140 and movement sensor 144. It may be arranged to disregard detection signals obtained when the user moves in a manner that may reduce the reliability of the detection signals below a predefined threshold.

Figure 6:
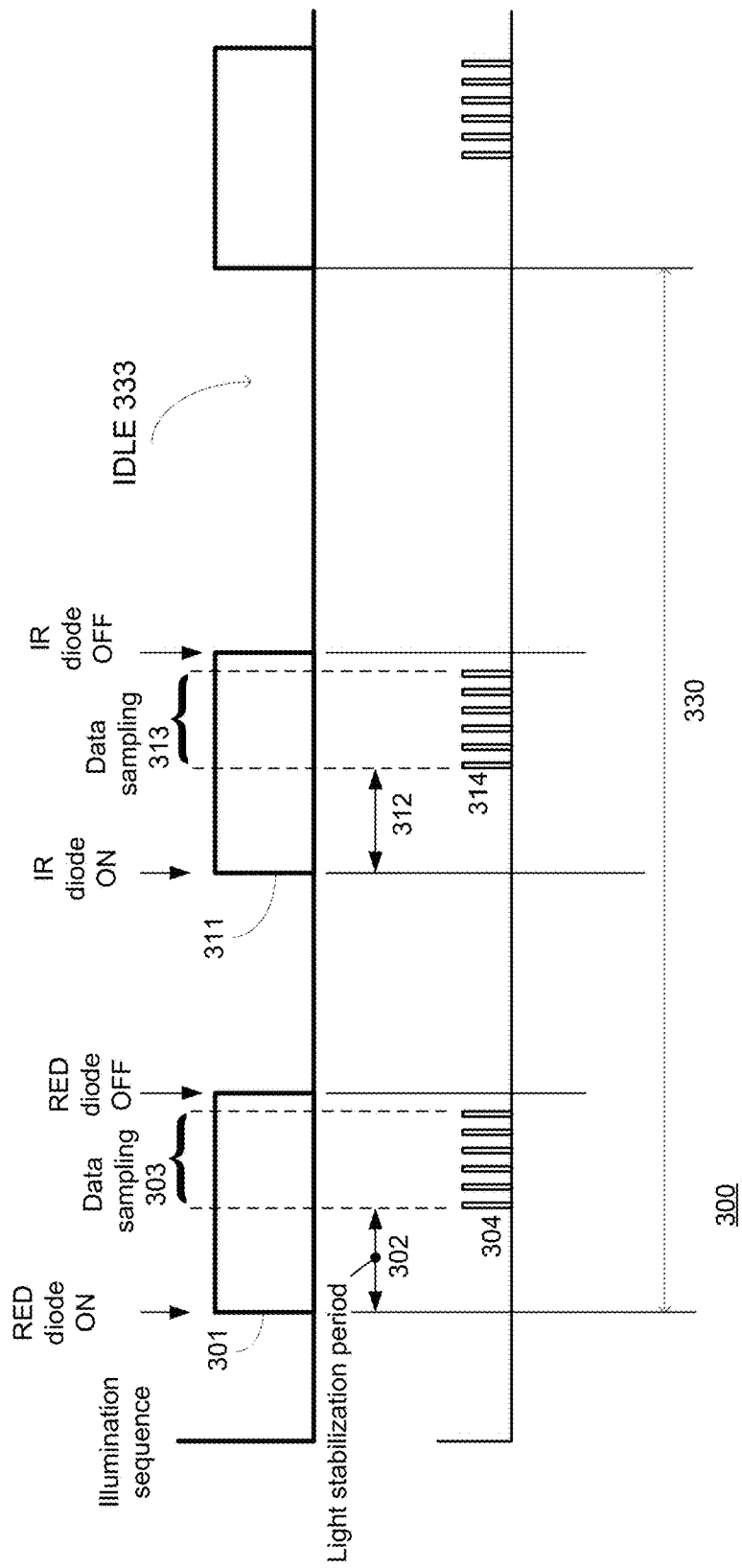
FIG. 6 is a timing diagram according to an embodiment of the invention.

FIG. 6 is a timing diagram 300 according to an embodiment of the invention. It illustrates a cyclic illumination pattern having a period of 330. Each cycle includes an activation window 301 of a red diode (delimited between RED diode ON and RED diode OFF) and an activation window 313 of an infrared diode (delimited between IR diode ON and IR diode OFF) that are followed by an idle period 333. Each activation window includes a stabilization period (302 and 312 respectively) in which the emitted light (red or infrared) is stabilized that is followed by a measurement period (303 and 313) in which the light pulses (304 and 314 respectively) can be used for oxygen saturation measurements. The activation windows may be of the same length (for example 0.5 millisecond) or of different lengths. The cyclic illumination pattern may have a cycle 330 that is longer and even much longer than the duration of the activation windows (for example—13 millisecond).

Detection signals generated during idle period 333 may be indicative of unwanted ambient light.

Figure 7:
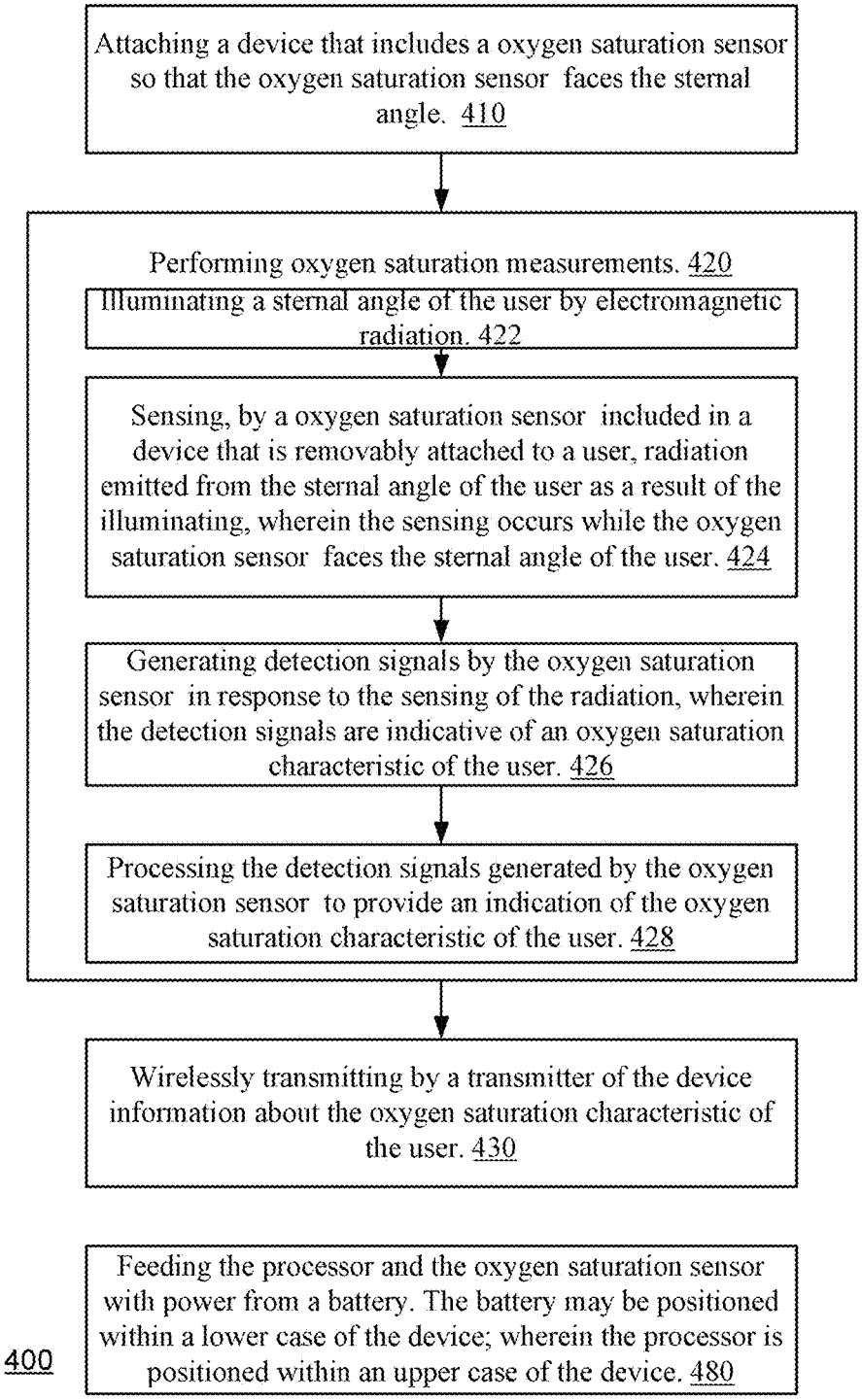
FIG. 7 illustrates a method according to an embodiment of the invention.

FIG. 7 illustrates method 400 according to an embodiment of the invention.

Method 400 may start by stage 410 of attaching a device that includes an oxygen saturation sensor so that the oxygen saturation sensor faces the sternal angle. This may, for example, positioning device 100 (or any other device that has an oxygen saturation sensor for sensing oxygen saturation characteristics) on a user. The device can be attached using a self-adhesive material, using a belt and the like.

Stage 410 may be followed by stage 420 of performing oxygen saturation measurements. Multiple oxygen saturation measurements can be performed over short or long periods of time-minutes, hours, days and even more.

An oxygen saturation measurement may include a detection signal acquisition phase and a processing phase. The detection signal acquisition phase is executed by the device attached to the client. The processing stage can be executed in full by the device, can be partially executed by the device or can be executed by another device or system not attached to the device.

The detection signal acquisition stage includes:
1. Illuminating (stage 422) a sternal angle of the user by electromagnetic radiation.
2. Sensing (stage 424) by an oxygen saturation sensor included in a device that is removably attached to a user, radiation emitted from the sternal angle of the user. The radiation detected can result from the illuminating of the sternal angle. The sensing occurs while the oxygen saturation sensor faces the sternal angle of the user.
3. Generating detection signals (stage 426) by the oxygen saturation sensor in response to the sensing of the radiation, wherein the detection signals are indicative of an oxygen saturation characteristic of the user.

Stage 422 may include illuminating the sternal angle of the user by a diode that emits visible light pulses and infrared pulses in an interleaved manner.

Stage 422 may be executed by an illumination module of the device.

Stage 424 may include sensing the radiation by one or more sensing elements such as photodiodes. If there are multiple sensing elements the sensing elements may be coupled to each other in parallel, in serial or a combination thereof.

Stage 424 may include sensing the radiation by a plurality of photodiodes that are arranged in a radially symmetrical manner.

The processing phase includes processing (stage 428) the detection signals generated by the oxygen saturation sensor to provide an indication of the oxygen saturation characteristic of the user.

If the processing is performed by a processor of the device then stage 428 is preceded (or includes) sending the detection signals to the processor of the device. If the processing is executed by a processor that does not belong to the device then the method includes transmitting the detection signals towards that processor.

Stage 420 may be followed by stage 430 of wirelessly transmitting by a transmitter of the device information about the oxygen saturation characteristic of the user.

Method 400 may also include stage 480 of feeding the processor and the oxygen saturation sensor with power from a battery. The battery may be positioned within a lower case of the device. The processor may be positioned within an upper case of the device.

Figure 8:
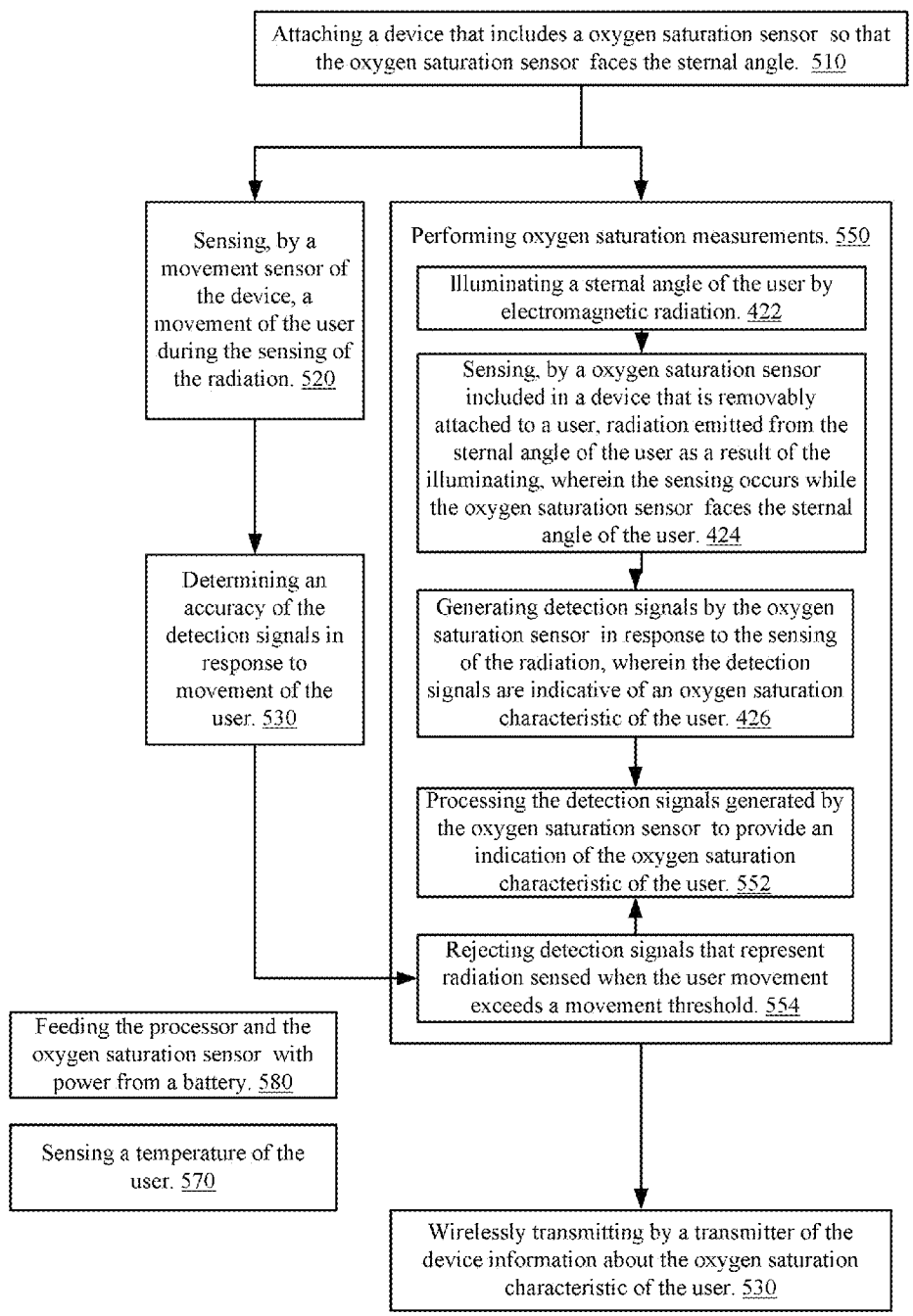
FIG. 8 illustrates a method according to an embodiment of the invention.

FIG. 8 illustrates method 500 according to an embodiment of the invention.

Method 500 starts by stage 510 of attaching a device that includes an oxygen saturation sensor so that the oxygen saturation sensor faces the sternal angle.

Stage 510 may be followed by stages 520 and 550.

Stage 520 may include sensing, by a movement sensor of the device, a movement of the user during the sensing of the radiation.

Stage 520 may be followed by stage 530 of determining an accuracy of the detection signals in response to movement of the user.

Stage 550 may include of performing oxygen saturation measurements. Multiple oxygen saturation measurements can be performed over short or long periods of time-minutes, hours, days and even more.

Stage 550 may include stages 422, 424 and 426. Stage 550 may also include stage 552 of processing the detection signals by the oxygen saturation sensor to provide an indication of the oxygen saturation characteristic of the user and stage 554 of rejecting detection signals that represent radiation sensed when the user movement exceeds a movement threshold.

If the processing is performed by a processor of the device then stage 552 is preceded (or includes) sending the detection signals to the processor of the device. If the processing is executed by a processor that does not belong to the device then the method includes transmitting the detection signals towards that processor.

Stage 550 may be followed by stage 560 of wirelessly transmitting by a transmitter of the device information about the oxygen saturation characteristic of the user.

Method 500 may also include stage 580 of feeding the processor and the oxygen saturation sensor with power from a battery. The battery may be positioned within a lower case of the device. The processor may be positioned within an upper case of the device.

FIG. 8 also illustrates method 500 as sensing (570) a temperature of the user by a temperature sensor of the device. It is noted that this stage can include performing any further sensing operation by any other type of sensor.

Figure 9:
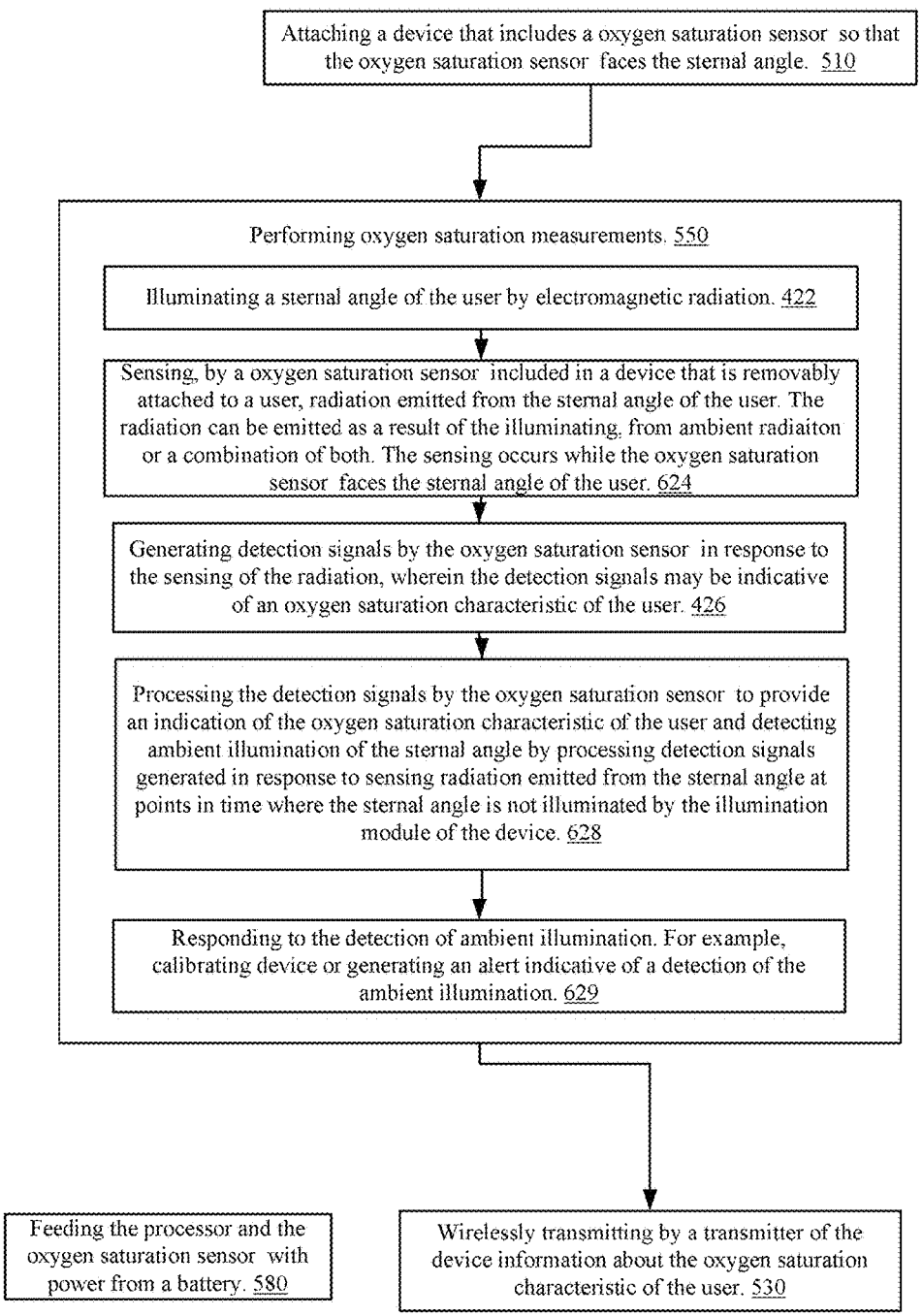
FIG. 9 illustrates a method according to an embodiment of the invention.

FIG. 9 illustrates method 600 according to an embodiment of the invention.

Method 600 may start by stage 610 of attaching a device that includes an oxygen saturation sensor so that the oxygen saturation sensor faces the sternal angle.

Stage 610 may be followed by stage 620 of performing oxygen saturation measurements.

An oxygen saturation measurement may include a detection signal acquisition phase and a processing phase. The detection signal acquisition phase is executed by the device attached to the client. The processing stage can be executed in full by the device, can be partially executed by the device or can be executed by another device or system not attached to the device.

The detection signal acquisition stage includes:
1. Illuminating (stage 422) a sternal angle of the user by electromagnetic radiation.
2. Sensing (stage 624), by an oxygen saturation sensor included in a device that is removably attached to a user, radiation emitted from the sternal angle of the user. The radiation detected can result of the illuminating of the sternal angle, from ambient illumination of from a combination thereof. The sensing occurs while the oxygen saturation sensor faces the sternal angle of the user.
3. Generating detection signals (stage 426) by the oxygen saturation sensor in response to the sensing of the radiation, wherein the detection signals are indicative of an oxygen saturation characteristic of the user.

Stage 424 may include sensing the radiation by one or more sensing elements such as photodiodes. If there are multiple sensing elements the sensing elements may be coupled to each other in parallel, in serial or a combination thereof.

The processing phase includes processing (stage 628) the detection signals by the oxygen saturation sensor to provide an indication of the oxygen saturation characteristic of the user.

Stage 628 may include detecting ambient illumination of the sternal angle by processing detection signals generated (during stage 426) in response to sensing radiation emitted from the sternal angle at points in time where the sternal angle is not illuminated by the illumination module of the device. See, for example, generation of detection signals that sense ambient radiation sensed during idle period 333 of FIG. 5.

Stage 628 may be followed by stage 629 of responding to the detection of ambient illumination.

For example, calibrating device or generating an alert indicative of a detection of the ambient illumination. The calibrating may include estimating the ambient light and compensating the oxygen saturation measurements in response to the ambient light. For example—reducing from detected radiation (detected when illuminating the sternum angle by IR or light pulse) the estimated value of the ambient light (IR component or light component respectively).

The alert may signal the user that he should re-attach the device in order to reduce or eliminate ambient radiation from reaching the sternum angle.

If the processing is performed by a processor of the device then stage 628 is preceded (or includes) sending the detection signals to the processor of the device. If the processing is executed by a processor that does not belong to the device then the method includes transmitting the detection signals towards that processor.

Stage 620 may be followed by stage 630 of wirelessly transmitting by a transmitter of the device information about the oxygen saturation characteristic of the user.

Method 600 may also include stage 680 of feeding the processor and the oxygen saturation sensor with power from a battery. The battery may be positioned within a lower case of the device. The processor may be positioned within an upper case of the device.

Figure 10:
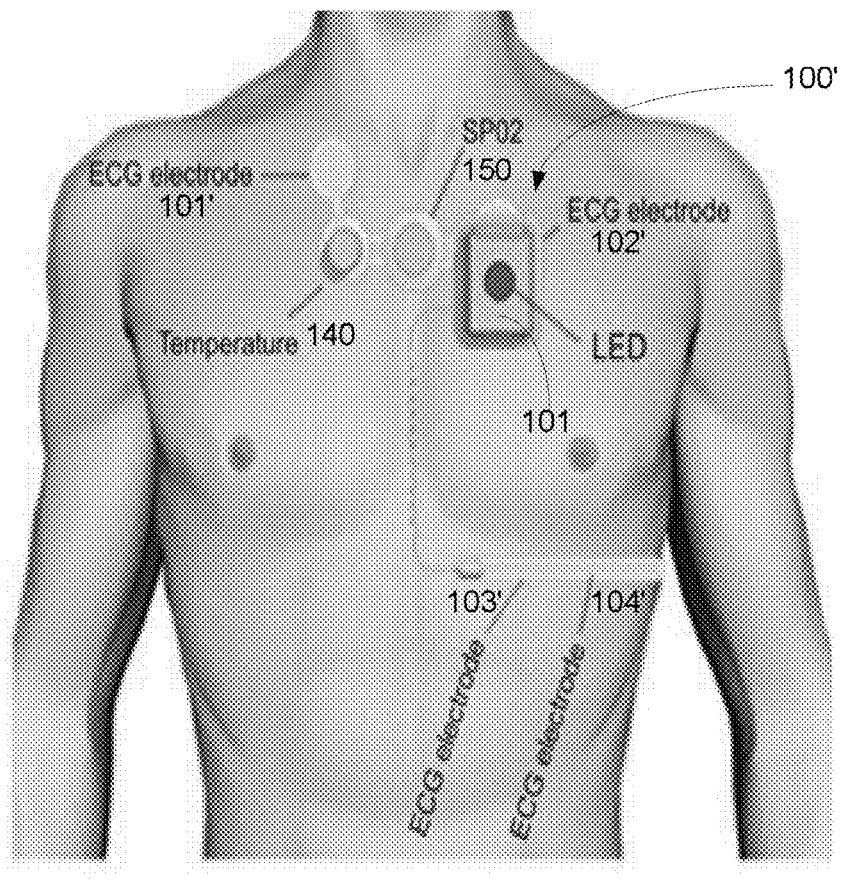
FIG. 10 illustrates a device that is removably attached to a person according to an embodiment of the invention.

FIG. 10 illustrates a device 100' that is removably attached to a person according to an embodiment of the invention.

The device 100' has a temperature sensor 140, an oxygen saturation sensor 150, processor and transceiver 101 and may be the device (denoted 100) that was illustrated in previous figures—but may differ from device 100.

Device 100' may include one or multiple electrocardiography (ECG) electrodes such as electrodes 101', 102', 103' and 104'.

It is desirable to aim the oxygen saturation sensor of the device 100' to illuminate the sternal angle of the person. This can be done by performing a positioning process.

Figure 11:
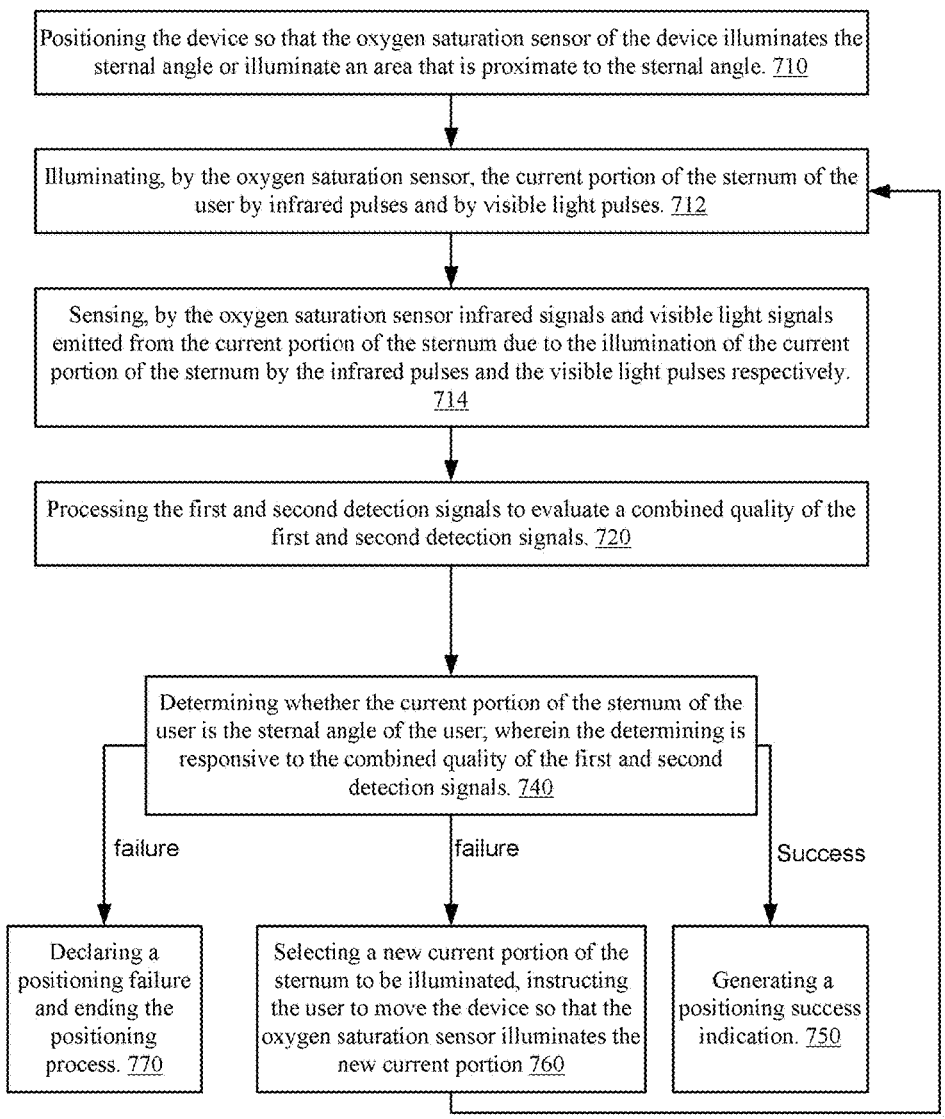
FIG. 11 illustrates a method for positioning the device according to an embodiment of the invention.

FIG. 11 illustrates a method 700 for positioning the device according to an embodiment of the invention.

Method 700 may start by stage 710 of positioning the device so that the oxygen saturation sensor of the device illuminates the sternal angle or illuminates an area that is proximate (for example by less than 10 centimeters) to the sternal angle. It may be assumed that the device is positioned so that the oxygen saturation sensor illuminates a current portion of the sternum of the user.

During a first execution of stage 710 the current portion is a first portion.

Stage 710 is followed by stage 712 of illuminating, by the oxygen saturation sensor, the current portion of the sternum of the user by infrared pulses and by visible light pulses. Pulses of different wavelength (infrared and visible light) may be transmitted towards the current portion of the sternum in a non-overlapping manner (at different points of time).

Stage 712 may be followed by stage 714 of sensing, by the oxygen saturation sensor, infrared signals and visible light signals emitted from the current portion of the sternum due to the illumination of the current portion of the sternum by the infrared pulses and the visible light pulses respectively.

Stage 714 may be followed by stage 716 of generating first and second detection signals, by the oxygen saturation sensor, in response to the sensing of the, infrared signals and visible light signals. The first and second detection signals are indicative of an oxygen saturation characteristic of the user.

The first detection signals are responsive to the infrared signals and the second detection signals are responsive to the visible light signals.

Stage 716 may be followed by stage 720 of processing the first and second detection signals to evaluate a quality of the first and second detection signals.

Stage 720 may be followed by stage 740 of determining whether the current portion of the sternum of the user is the sternal angle of the user; wherein the determining is responsive to the quality of the first and second detection signals.

Stage 740 may include determining that the current portion of the sternum of the user is the sternal angle of the user if the quality of the first and second detection signals exceeds a predetermined quality threshold.

Stage 720 and/or step 740 may be executed by the oxygen saturation sensor, by a computerized device that includes the oxygen saturation sensor, or by a computerized device that does not include the oxygen saturation sensor or may be executed in part by the oxygen saturation sensor and in part by the computerized device that does not include the oxygen saturation sensor.

If it is determined that the current portion of the sternum of the user is the sternal angle of the user than stage 740 may be followed by stage 750 of generating a positioning success indication.

The positioning success indication may be sent to the user, to a user device or to a third party. The aim of the positioning success indication is to notify the user or a third party that the device should be positioned so that the oxygen saturation sensor illuminates the sternal angle of the user. The positioning may include peeling a protective element and detachably connecting the device to the user.

If it is determined that the current portion of the sternum of the user is not the sternal angle of the user than stage 740 may be followed by stage 760 of selecting a new current portion of the sternum to be illuminated, instructing the user to move the device so that the oxygen saturation sensor illuminates the new current portion and repeating stages 712, 714, 716, 720 and 740 for the new current portion.

It is also noted that if it is determined that the current portion of the sternum of the user is not the sternal angle of the user then stage 740 may be followed by stage 770 of declaring a positioning failure and ending the positioning process.

According to another embodiment of the invention stages 712, 714, 716, 720, 740 and 760 are repeated multiple times to find one or more current portions of the sternum that are valid candidates of a sternal angle—and selecting the best current portions of the one or more valid candidates—for example selecting the valid candidate with the highest quality. Each valid candidate may have a quality that exceeds a valid candidate quality threshold. The valid candidate quality threshold may not exceed the predetermined quality threshold.

Figure 12:
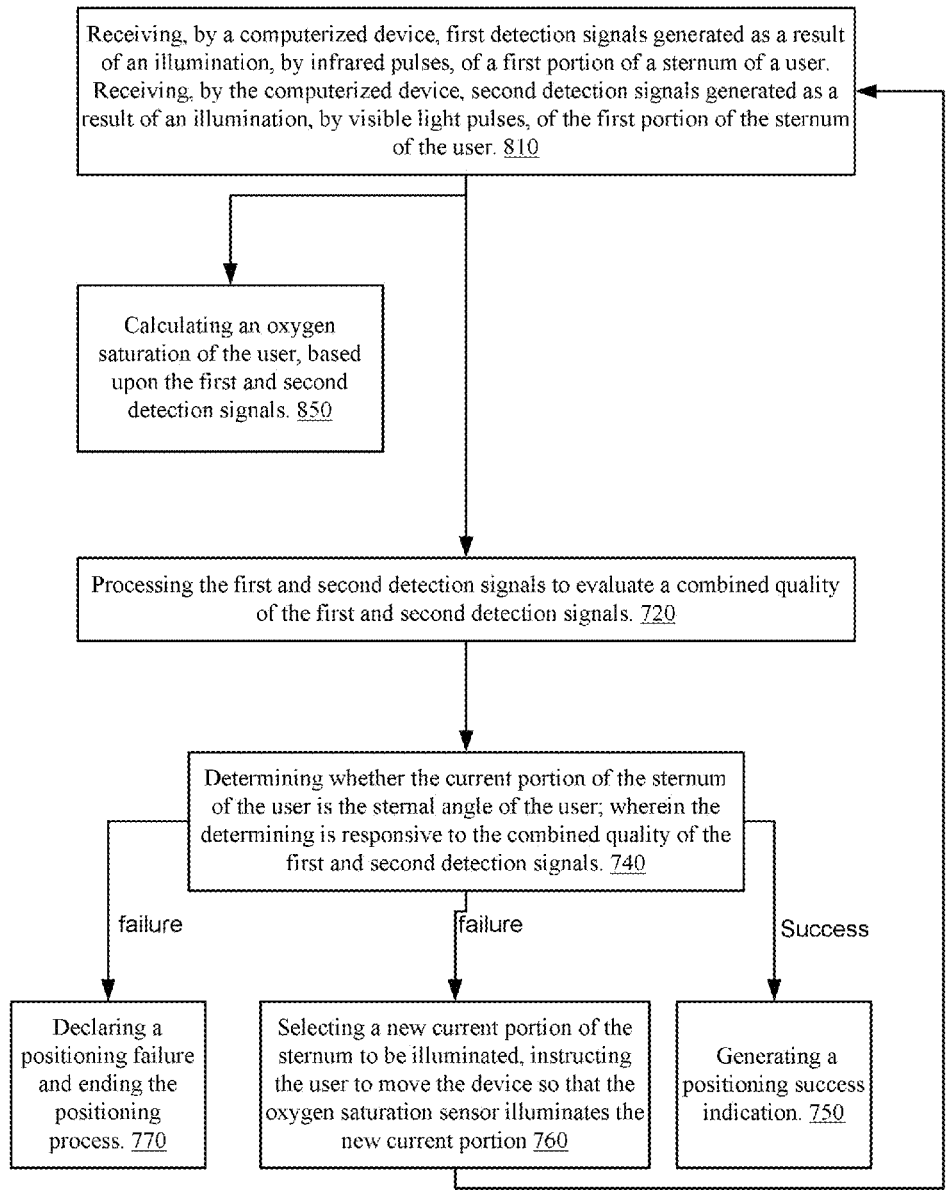
FIG. 12 illustrates a method according to an embodiment of the invention.

FIG. 12 illustrates a method 800 according to an embodiment of the invention.

Method 800 is executed by a computerized device.

Method 800 starts by stage 810 of (a) receiving, by a computerized device, first detection signals generated as a result of an illumination, by infrared pulses, of a first portion of a sternum of a user; and (b) receiving, by the computerized device, second detection signals generated as a result of an illumination, by visible light pulses, of the first portion of the sternum of the user;

Stage 810 is followed by stage 720 of processing the first and second detection signals to evaluate a quality of the first and second detection signals.

Stage 720 may be followed by stage 740 of determining whether the current portion of the sternum of the user is the sternal angle of the user. The determining may be responsive to the quality of the first and second detection signals. Stage 740 may be followed by stage 750, 760 or 770.

Stage 810 may be followed by stage 850 of calculating an oxygen saturation of the user, based upon the first and second detection signals.

Differences between amplitudes of infrared signals and visible light signals emitted from the user are indicative of the oxygen saturation of the user. Especially—the ratio between the amplitudes of infrared signals and the visible light signals detected by the oxygen saturation sensor is indicative of the oxidation level of the blood of the user.

Figure 13:
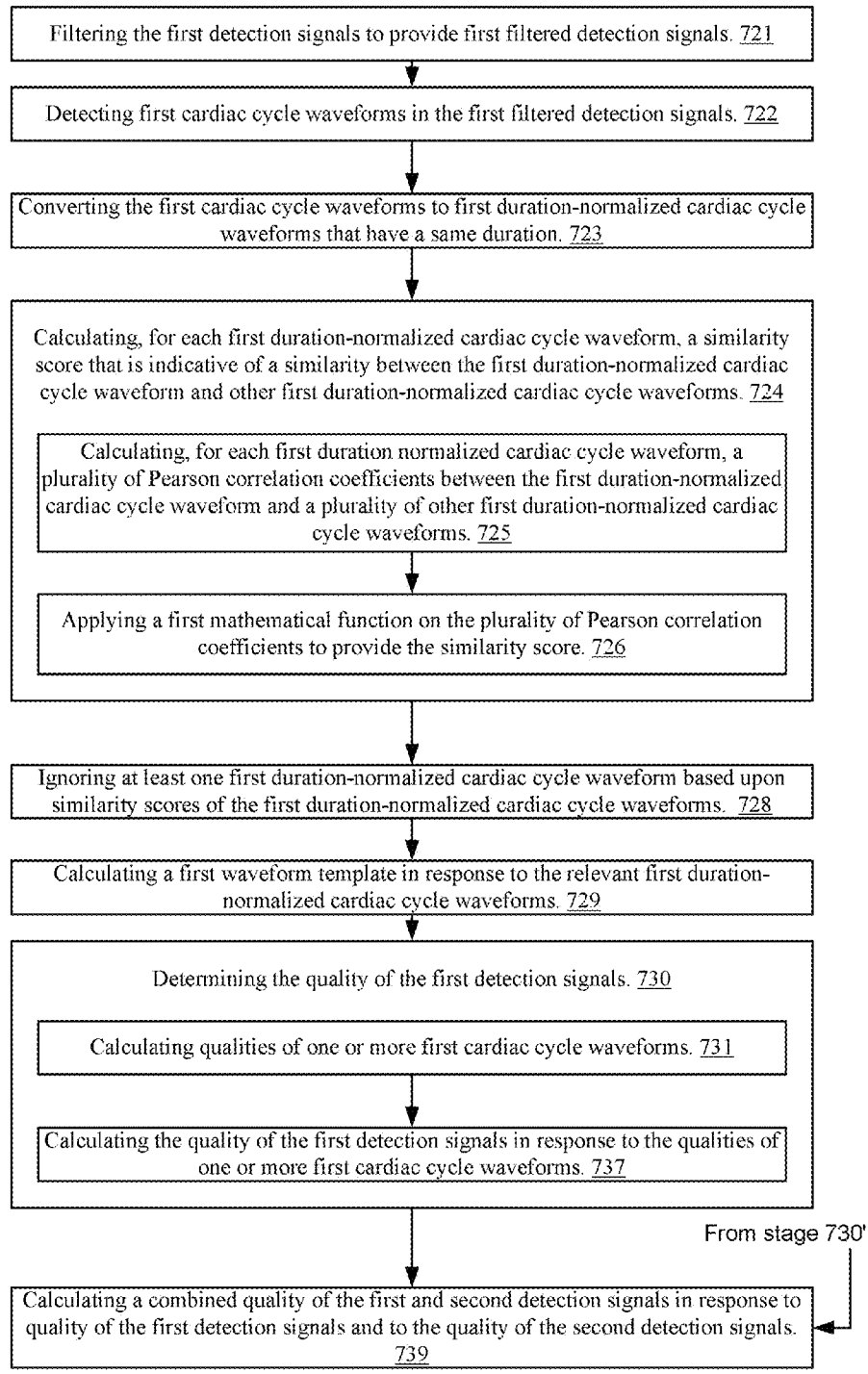
Figure 14:
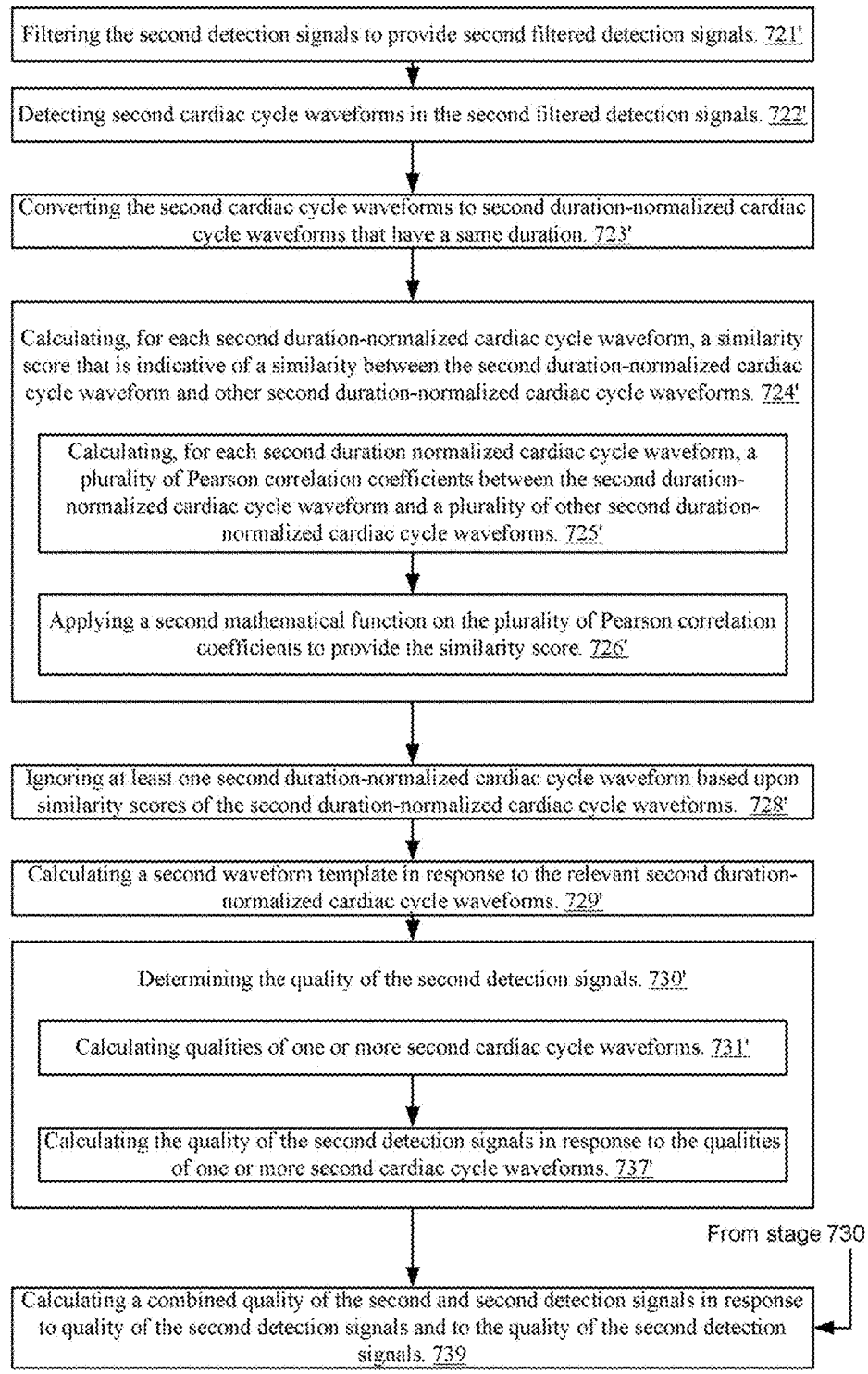

FIGS. 13-15 illustrate stage 720 of processing the first and second detection signals to evaluate a quality of the first and second detection signals according to an embodiment of the invention.

Stage 720 may include at least one of the following stages. For simplicity of explanation it is assumed that stage 720 includes all of the following stages, although stage 720 may include only one or some of the following stages.

Stage 720 may start by stages 721 and 721'.

Stage 721 may include filtering the first detection signals to provide first filtered detection signals. The filtering may include high-pass filtering and low-pass filtering or applying bandpass filtering. The low-pass filtering may be bilateral filtering, any other edge preserving filtering or any other filtering.

Stage 721 may be followed by stage 722 of detecting first cardiac cycle waveforms in the first filtered detection signals.

Stage 722 may be followed by stage 723 of converting the first cardiac cycle waveforms to first duration-normalized cardiac cycle waveforms that have a same duration.

Stage 723 may be followed by stage 724 of calculating, for each first duration-normalized cardiac cycle waveform, a similarity score that is indicative of a similarity between the first duration-normalized cardiac cycle waveform and other first duration-normalized cardiac cycle waveforms.

Stage 724 may include stage 725 of calculating, for each first duration normalized cardiac cycle waveform, a plurality of Pearson correlation coefficients between the first duration-normalized cardiac cycle waveform and a plurality of other first duration-normalized cardiac cycle waveforms. The plurality of other first duration-normalized cardiac cycle waveforms may include all of the first duration-normalized cardiac cycle waveforms that differ from the first duration normalized cardiac cycle waveform or only some of these other first duration-normalized cardiac cycle waveforms.

For example, a Pearson correlation coefficient ($R_{ij}$) between an i'th first duration-normalized cardiac cycle waveform ($w_i$) and a j'th first duration-normalized cardiac cycle waveform ($w_j$) may be expressed by the following equation:

$$R_{i,j} = \text{covariance}(w_i, w_j)/std(w_i)*std(w_j).$$

Wherein "std" stands for a standard deviation.

Stage 725 may be followed by stage 726 (may also be included in stage 724) of applying a first mathematical function on the plurality of Pearson correlation coefficients to provide the similarity score. The applying may include, for example, summing the plurality of Pearson correlation coefficients to provide the similarity score.

Stage 724 may be followed by stage 728 of ignoring at least one first duration-normalized cardiac cycle waveform based upon similarity scores of the first duration-normalized cardiac cycle waveforms. Stage 728 provides relevant first duration-normalized cardiac cycle waveforms (those first duration-normalized cardiac cycle waveform that were not ignored of).

Stage 728 may include, for example, ignoring one or more first duration-normalized cardiac cycle waveform that have a similarity score that is below a similarity score threshold, ignoring a preset number of first duration-normalized cardiac cycle waveforms that have the lowest similarity scores, and the like.

Stage 728 may be followed by stage 729 of calculating a first waveform template in response to the relevant first duration-normalized cardiac cycle waveforms. This stage may include applying a second mathematical function on the relevant first duration-normalized cardiac cycle waveforms. The second mathematical function may be any mathematical function. If may be, for example. A weighted averaging function, an averaging function and the like.

Stage 729 may be followed by stage 730 of determining the quality of the first detection signals.

Stage 730 may include stage 731 of calculating qualities of one or more first cardiac cycle waveforms. These one or more first cardiac cycle waveforms may include all the first cardiac cycle waveforms detected during stage 722 or only some of the first cardiac cycle waveforms detected during stage 722. For example—the one or more first cardiac cycle waveforms may correspond to the relevant first duration-normalized cardiac cycle waveforms.

Stage 731 may include at least one out of stages 732, 733, 734, 735 and 736. For example, stage 731 may include stages 734, 735 and 736.

Stage 732 may include comparing the first cardiac cycle waveforms to the first waveform template.

Stage 733 may include calculating correlations between shapes of the at least some of the first cardiac cycle waveforms and a shape of the first waveform template.

Stage 734 may include converting at least some of the first cardiac cycle waveforms to first duration-normalized and peak-normalized cardiac cycle waveforms and calculating relationships between shapes of the first duration-normalized and peak-normalized cardiac cycle waveforms and a shape of the first waveform template. The first duration-normalized and peak-normalized cardiac cycle waveforms are a same duration and a same peak value as the first waveform template.

Stage 735 may include calculating relationships between peaks of the at least some of the first cardiac cycle waveforms and a peak of the first waveform template.

Stage 736 may include calculating relationships between durations of the at least some of the first cardiac cycle waveforms and a duration of the first waveform template quality of the first detection signals.

Stage 730 may include stage 737 of calculating the quality of the first detection signals in response to the qualities (calculated during stage 731) of one or more first cardiac cycle waveforms.

Stage 721' may include filtering the second detection signals to provide second filtered detection signals. The filtering may include high-pass filtering and low-pass filtering or applying bandpass filtering. The low-pass filtering may be bilateral filtering, any other edge preserving filtering or any other filtering.

Stage 721' may be followed by stage 722' of detecting second cardiac cycle waveforms in the second filtered detection signals.

Stage 722' may be followed by stage 723' of converting the second cardiac cycle waveforms to second duration-normalized cardiac cycle waveforms that have a same duration.

Stage 723' may be followed by stage 724' of calculating, for each second duration-normalized cardiac cycle waveform, a similarity score that is indicative of a similarity between the second duration-normalized cardiac cycle waveform and other second duration-normalized cardiac cycle waveforms.

Stage 724' may include stage 725' of calculating, for each second duration normalized cardiac cycle waveform, a plurality of Pearson correlation coefficients between the second duration-normalized cardiac cycle waveform and a plurality of other second duration-normalized cardiac cycle waveforms. The plurality of other second duration-normalized cardiac cycle waveforms may include all of the second duration-normalized cardiac cycle waveforms that differ from the second duration normalized cardiac cycle waveform or only some of these other second duration-normalized cardiac cycle waveforms.

Stage 725' may be followed by stage 726' (may also be included in stage 724') of applying a first mathematical function on the plurality of Pearson correlation coefficients to provide the similarity score. The applying may include, for example, summing the plurality of Pearson correlation coefficients to provide the similarity score.

Stage 724' may be followed by stage 728' of ignoring at least one second duration-normalized cardiac cycle waveform based upon similarity scores of the second duration-normalized cardiac cycle waveforms. Stage 728' provides relevant second duration-normalized cardiac cycle waveforms (those second duration-normalized cardiac cycle waveform that were not ignored of).

Stage 728' may include, for example, ignoring one or more second duration-normalized cardiac cycle waveform that have a similarity score that is below a similarity score threshold, ignoring a preset number of second duration-normalized cardiac cycle waveforms that have the lowest similarity scores, and the like.

Stage 728' may be followed by stage 729' of calculating a second waveform template in response to the relevant second duration-normalized cardiac cycle waveforms. This stage may include applying a second mathematical function on the relevant second duration-normalized cardiac cycle waveforms. The second mathematical function may be any mathematical function. If may be, for example. A weighted averaging function, an averaging function and the like.

Stage 729' may be followed by stage 730' of determining the quality of the second detection signals.

Stage 730' may include stage 731' of calculating qualities of one or more second cardiac cycle waveforms. These one or more second cardiac cycle waveforms may include all the second cardiac cycle waveforms detected during stage 722' or only some of the second cardiac cycle waveforms detected during stage 722'. For example—the one or more second cardiac cycle waveforms may correspond to the relevant second duration-normalized cardiac cycle waveforms.

Stage 731' may include at least one out of stages 732', 733', 734', 735' and 736'. For example, stage 731' may include stages 734, 735' and 736'.

Stage 732' may include comparing the second cardiac cycle waveforms to the second waveform template.

Stage 733' may include calculating correlations between shapes of the at least some of the second cardiac cycle waveforms and a shape of the second waveform template.

Stage 734' may include converting at least some of the second cardiac cycle waveforms to second duration-normalized and peak-normalized cardiac cycle waveforms and calculating relationships between shapes of the second duration-normalized and peak-normalized cardiac cycle waveforms and a shape of the second waveform template. The second duration-normalized and peak-normalized cardiac cycle waveforms are a same duration and a same peak value as the second waveform template.

Stage 735' may include calculating relationships between peaks of the at least some of the second cardiac cycle waveforms and a peak of the second waveform template.

Stage 736' may include calculating relationships between durations of the at least some of the second cardiac cycle waveforms and a duration of the second waveform template quality of the second detection signals.

Stage 730' may include stage 737' of calculating the quality of the second detection signals in response to the qualities (calculated during stage 731') of one or more second cardiac cycle waveforms.

Stages 730 and 730' may be followed by stage 739 of calculating a quality of the first and second detection signals in response to quality of the first detection signals and to the quality of the second detection signals. Stage 739 may include summing, weighted summing, averaging or applying any function on the quality of the first detection signals and the quality of the second detection signals.

Figure 16:
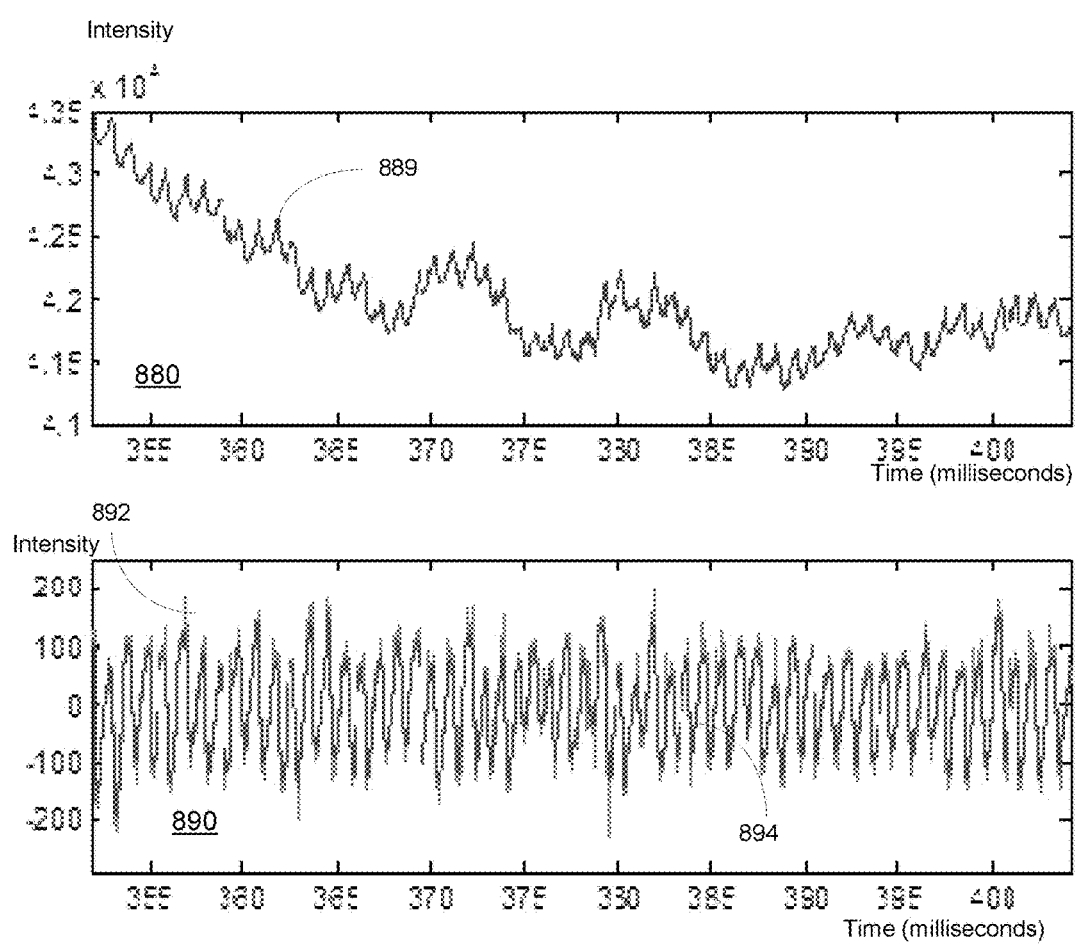
FIG. 16 illustrates first detection signals and first filtered detection signals according to an embodiment of the invention.

FIG. 16 illustrates first detection signals 882 and first filtered detection signals according to an embodiment of the invention.

Graph 880 of FIG. 16 illustrates first detection signals 882.

Graph 890 of FIG. 16 illustrates first filtered detection signals 892 and 894. First filtered detection signals 892 were filtered only by a high-pass filter (a Butterworth high-pass filter) while first filtered detection signals 894 were filtered using both a high-pass filter and a low-pass (Bilateral) filter.

The x-axis of graphs 880 and 890 represent time while the y-axis of graphs 880 and 890 represent intensity.

Figure 17:
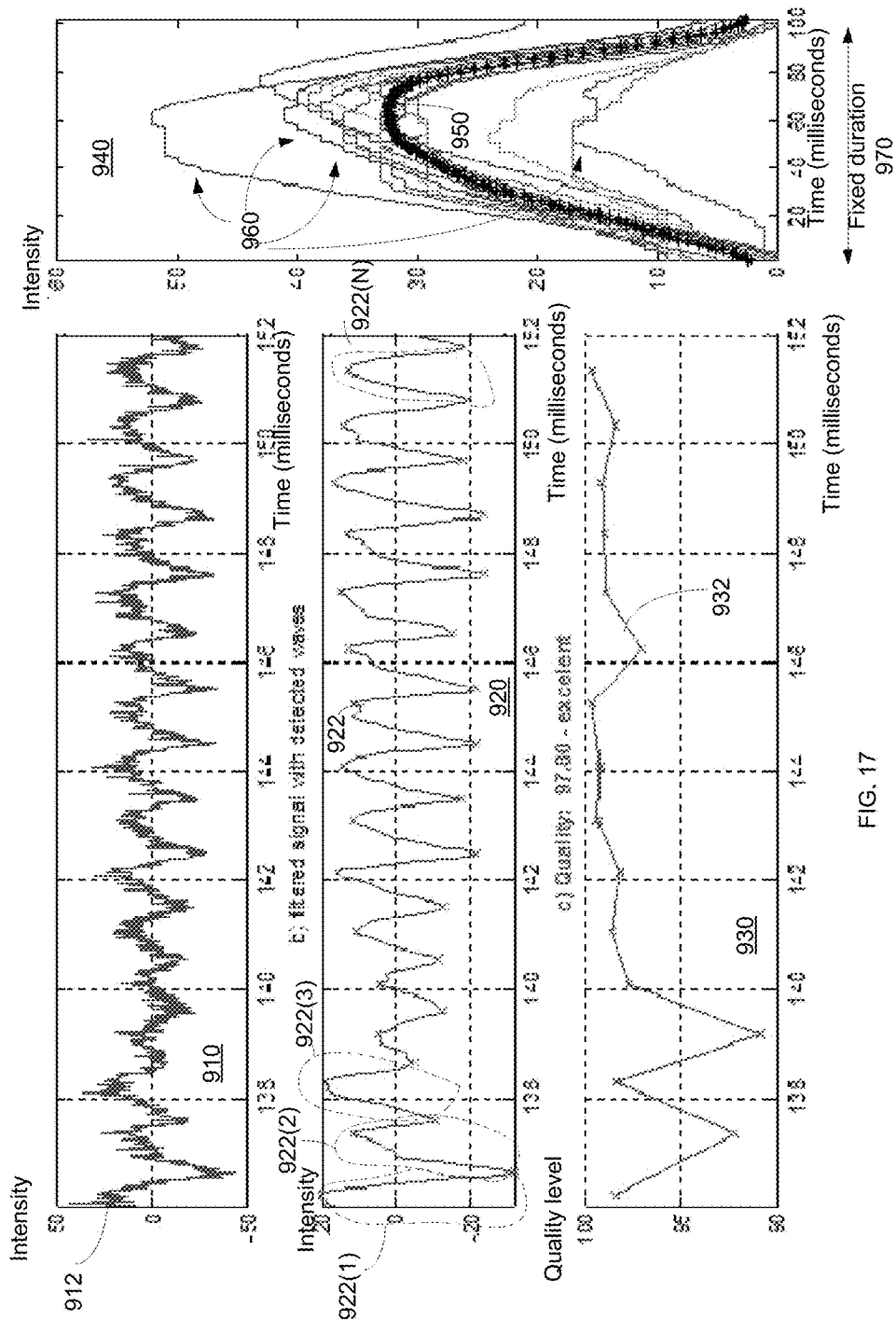
FIG. 17 illustrates first detection signals, first filtered detection signals, first cardiac cycle waveforms, first waveform template, first duration-normalized cardiac cycle waveforms of a fixed duration, and first cardiac cycle waveform quality scores 932 according to an embodiment of the invention.

FIG. 17 illustrates first detection signals 912, first filtered detection signals 922, first cardiac cycle waveforms 922(1)-922(N), first waveform template 950 and first duration-normalized cardiac cycle waveforms 960 of a fixed duration 970, and first cardiac cycle waveform quality scores 932 according to an embodiment of the invention.

Graph 910 of FIG. 17 illustrates first detection signals 912.

Graph 920 of FIG. 17 illustrates first filtered detection signals 922 that include first cardiac cycle waveforms 922(1)-922(N).

Graph 930 of FIG. 17 illustrates first cardiac cycle waveform quality scores 932 of first cardiac cycle waveforms 922(1)-922(N).

Graph 940 of FIG. 17 illustrates first waveform template 950, first duration-normalized cardiac cycle waveforms 960 of a fixed duration 970. The first cardiac cycle waveforms were converted to become the first duration-normalized cardiac cycle waveforms 960.

The x-axis of graphs 910, 920, 930 and 940 represent time while the y-axis of graphs 910, 920 and 940 represent intensity.

FIG. 18 illustrates method 1000 according to an embodiment of the invention.

Method 1000 may start by stage 1010 of receiving, by a computerized device, first and second detection signals and electrocardiograph signals. The first detection signals result from an illumination, by an oxygen saturation sensor included in a device that is removably attached to a user, of a sternal angle of a user by infrared pulses. The second detection signals result from an illumination, by the oxygen saturation sensor, of the sternal angle of a user by visible light pulses. The electrocardiograph signals are detected by an electrocardiography sensor that is included in the device.

Stage 1010 may be followed by stages 1020, 1030, 1040, 1050 and 1060.

Stage 1020 may include generating a first waveform template that is responsive to the first detection signals.

Stage 1020 may include at least one of stages 721-726, 728 and 729 of FIG. 13.

Stage 1030 may include generating a second waveform template that is responsive to the second detection signals.

Stage 1030 may include at least one of stages 721'-726', 728' and 729' of FIG. 14.

Stage 1040 may include calculating an indication of the oxygen saturation characteristic of the user in response to the first and second detection signals.

Stage 1050 may include detecting cardiac cycle durations that are based upon the first and second detection signals.

Stage 1050 may include stages 721, 722, 721' and 722' of FIGS. 13 and 14.

Stage 1060 may include detecting electrocardiography based cardiac cycle durations.

Stages 1020, 1030, 1040, 1050 and 1060 may be followed by stage 1070 of evaluating a quality of the indication of the oxygen saturation characteristic of the user in response to the first waveform template, the second waveform template, the cardiac cycle's durations and the electrocardiography based cardiac cycle durations.

Stage 1070 may include at least one of stages 730, 731, 732, 733, 734, 735, 736, 737, 730', 731', 732', 733', 734', 735', 736', 737' and 739'.

Figure 19:
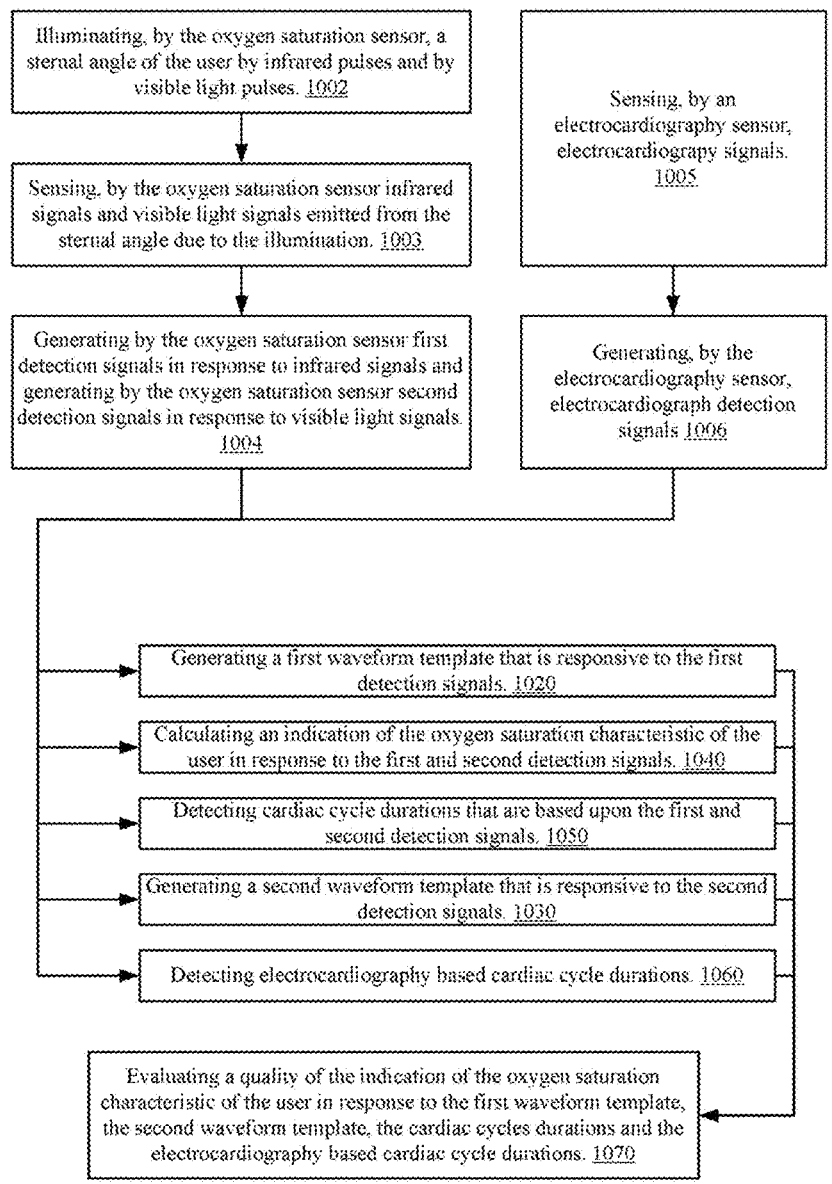
FIG. 19 illustrates a method according to an embodiment of the invention.

FIG. 19 illustrates method 1000' according to an embodiment of the invention.

Method 1000' may start by stages 1002 and 1005.

Stage 1002 may include illuminating, by the oxygen saturation sensor, a sternal angle of the user by infrared pulses and by visible light pulses.

Stage 1002 may be followed by stage 1003 of sensing, by the oxygen saturation sensor infrared signals and visible light signals emitted from the sternal angle due to the illumination.

Stage 1003 may be followed by stage 1004 of generating by the oxygen saturation sensor first detection signals in response to infrared signals and generating by the oxygen saturation sensor second detection signals in response to visible light signals.

Stage 1005 may include sensing, by an electrocardiography sensor, electrocardiography signals.

Stage 1005 may be followed by stage 1006 of generating, by the electrocardiography sensor, electrocardiograph detection signals.

Stages 1004 and 1002 may be executed in parallel to each other, in a partially overlapping manner or in a non-overlapping manner. The method can benefit from sensing the same cardiac cycles by the oxygen saturation sensor and the electrocardiography sensor.

Stage 1004 and stage 1006 may be followed by stages 1020, 1030, 1040, 1050 and 1060.

Stage 1020 may include generating a first waveform template that is responsive to the first detection signals.

Stage 1030 may include generating a second waveform template that is responsive to the second detection signals.

Stage 1040 may include calculating an indication of the oxygen saturation characteristic of the user in response to the first and second detection signals.

Stage 1050 may include detecting cardiac cycle durations that are based upon the first and second detection signals.

Stage 1060 may include detecting electrocardiography based cardiac cycle durations.

Stages 1020, 1030, 1040, 1050 and 1060 may be followed by stage 1070 of evaluating a quality of the indication of the oxygen saturation characteristic of the user in response to the first waveform template, the second waveform template, the cardiac cycle's durations and the electrocardiography based cardiac cycle durations.

Figure 20:
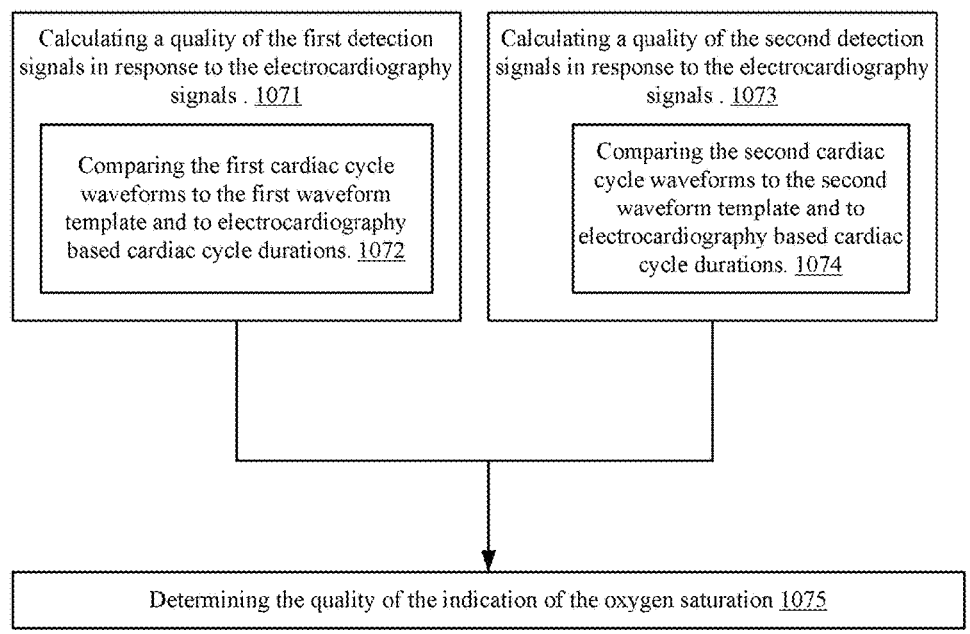
FIG. 20 illustrates a stage according to an embodiment of the invention.

FIG. 20 illustrates stage 1070 according to an embodiment of the invention.

Stage 1070 may start by stages 1071 and 1073.

Stage 1071 may include calculating a quality of the first detection signals in response to the electrocardiography signals.

Stage 1071 may include stage 1072 of comparing the first cardiac cycle waveforms to the first waveform template and to electrocardiography based cardiac cycle durations.

Stage 1073 may include calculating a quality of the second detection signals in response to the electrocardiography signals.

Stage 1073 may include stage 1074 may include comparing the second cardiac cycle waveforms to the second waveform template and to electrocardiography based cardiac cycle durations.

Stage 1071 and 1073 may be followed by stage 1075 of determining the quality of the indication of the oxygen saturation. This may include applying any function on the quality of the first detection signals and (b) the quality of the second detection signals.

Figure 21:
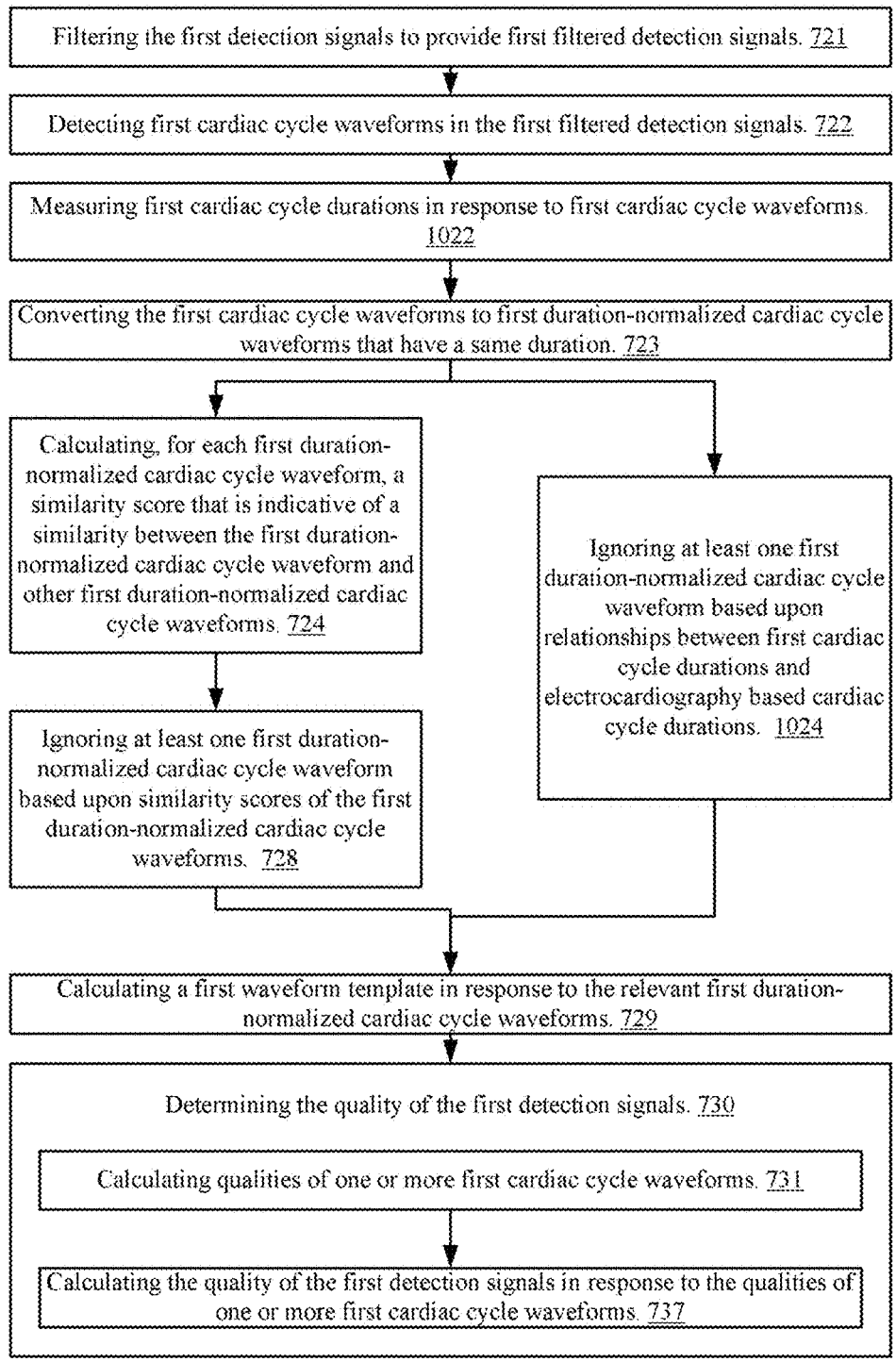
FIG. 21 illustrates a stage for calculating a quality of the first detection signals in response to the electrocardiography signals according to an embodiment of the invention.

FIG. 21 illustrates a stage 1071 for calculating a quality of the first detection signals in response to the electrocardiography signals according to an embodiment of the invention.

Stage 721 may include filtering the first detection signals to provide first filtered detection signals. The filtering may include high-pass filtering and low-pass filtering or applying bandpass filtering. The low-pass filtering may be bilateral filtering, any other edge preserving filtering or any other filtering.

Stage 721 may be followed by stage 722 of detecting first cardiac cycle waveforms in the first filtered detection signals.

Stage 722 may be followed by stage 723 of converting the first cardiac cycle waveforms to first duration-normalized cardiac cycle waveforms that have a same duration.

Stage 723 may be followed by one or more branches. A first branch (also shown in FIG. 13) includes stages 724 and 728 and a second branch includes stage 1024. Both branches are followed by stage 729.

Stage 1024 may include ignoring at least one first duration-normalized cardiac cycle waveform based upon relationships between first cardiac cycle durations and electrocardiography based cardiac cycle durations.

Stage 724 may include calculating, for each first duration-normalized cardiac cycle waveform, a similarity score that is indicative of a similarity between the first duration-normalized cardiac cycle waveform and other first duration-normalized cardiac cycle waveforms.

Stage 724 may include stages (not shown) such as stages 725 and 726 of FIG. 13.

Stage 724 may be followed by stage 728 of ignoring at least one first duration-normalized cardiac cycle waveform based upon similarity scores of the first duration-normalized cardiac cycle waveforms. Stage 728 provides relevant first duration-normalized cardiac cycle waveforms (those first duration-normalized cardiac cycle waveform that were not ignored of).

Stage 728 may include, for example, ignoring one or more first duration-normalized cardiac cycle waveform that have a similarity score that is below a similarity score threshold, ignoring a preset number of first duration-normalized cardiac cycle waveforms that have the lowest similarity scores, and the like.

Stage 729 may include calculating a first waveform template in response to the relevant first duration-normalized cardiac cycle waveforms. This stage may include applying a second mathematical function on the relevant first duration-normalized cardiac cycle waveforms. The second mathematical function may be any mathematical function. If may be, for example. A weighted averaging function, an averaging function and the like.

Stage 729 may be followed by stage 730 of determining the quality of the first detection signals.

Stage 730 may include stage 731 of calculating qualities of one or more first cardiac cycle waveforms. These one or more first cardiac cycle waveforms may include all the first cardiac cycle waveforms detected during stage 722 or only some of the first cardiac cycle waveforms detected during stage 722. For example—the one or more first cardiac cycle waveforms may correspond to the relevant first duration-normalized cardiac cycle waveforms.

Stage 731 may include at least one out of stages (not shown in FIG. 21 but illustrated in FIGS. 13) 732, 733, 734, 735 and 736.

Stage 730 may include stage 737 of calculating the quality of the first detection signals in response to the qualities (calculated during stage 731) of one or more first cardiac cycle waveforms.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for measuring oxygen saturation of a user, the method comprises:
   receiving, by a computerized device, first and second detection signals and electrocardiograph signals;
      wherein the first detection signals result from an illumination by infrared pulses of a sternal angle of a user, and being detected by an oxygen saturation sensor included in a device that is removably attached to a user;
      wherein the second detection signals result from an illumination by visible light pulses detected by the oxygen saturation sensor, of the sternal angle of a user;
      wherein the electrocardiograph signals are detected by an electrocardiography sensor that is included in the device;
   generating a first waveform template by analyzing the second detection signals to normalize the second detection signals and identify cardiac cycle duration characteristics of the second detection signals that are substantially consistent within the second detection signals;
   calculating an indication of the oxygen saturation characteristic of the user in response to the first and second detection signals;
   detecting cardiac cycle durations that are based upon the first and second detection signals;
   detecting electrocardiography based cardiac cycle durations; and
   evaluating a quality of the indication of the oxygen saturation characteristic of the user by comparing the first waveform template to the electrocardiography based cardiac cycle durations.

2. The method according to claim 1 comprising applying a high-pass filter and a bilateral filter on the first detection signals to provide first filtered detection signals.

3. The method according to claim 1 wherein the generating of the first waveform template comprises filtering the first detection signals to provide first filtered detection signals; and detecting first cardiac cycle waveforms in the first filtered detection signals.

4. The method according to claim 3 wherein the detecting of the cardiac cycle durations comprises measuring durations of the first cardiac cycle waveforms.

5. The method according to claim 3 wherein the generating of the first waveform template comprises converting the first cardiac cycle waveforms to first duration-normalized cardiac cycle waveforms that have a same duration.

6. The method according to claim 5 wherein the generating of the first waveform template is responsive to at least some of the first duration-normalized cardiac cycle waveforms.

7. The method according to claim 5 wherein the generating of the first waveform template equals an average of at least some of the first duration-normalized cardiac cycle waveforms.

8. The method according to claim 5 wherein the generating of the first waveform template further comprises calculating, for each first duration-normalized cardiac cycle waveform, a similarity score indicative of a similarity between the first duration-normalized cardiac cycle waveform and other first duration-normalized cardiac cycle waveforms.

9. The method according to claim 8 wherein the generating of the first waveform template further comprises ignoring at least one first duration-normalized cardiac cycle waveform based upon similarity scores of the first duration-normalized cardiac cycle waveforms.

10. The method according to claim 8 wherein the calculating, for each first duration-normalized cardiac cycle waveform, of the similarity score comprises calculating a plurality of Pearson correlation coefficients between the first duration-normalized cardiac cycle waveform and a plurality of other first duration-normalized cardiac cycle waveforms.

11. The method according to claim 10 wherein the calculating, for each first duration-normalized cardiac cycle waveform, of the similarity score comprises summing the plurality of Pearson correlation coefficients.

12. The method according to claim 3 comprising calculating qualities of at least some of the first cardiac cycle waveforms; and wherein the quality of the first and second detection signals is responsive to the qualities of the at least some of the first cardiac cycle waveform.

13. The method according to claim 12 wherein the calculating of the qualities of at least some of the first cardiac cycle waveforms comprises comparing the at least some of the first cardiac cycle waveforms to the first waveform template.

14. The method according to claim 12 wherein the calculating of the qualities of at least some of the first cardiac cycle waveforms comprises calculating correlations between shapes of the at least some of the first cardiac cycle waveforms and a shape of the first waveform template.

15. The method according to claim 12 wherein the calculating of the qualities of at least some of the first cardiac cycle waveforms comprises converting at least some of the first cardiac cycle waveforms to first duration-normalized and peak-normalized cardiac cycle waveforms and a shape of the first waveform template; and wherein the first duration-normalized and peak-normalized cardiac cycle waveforms are a same duration and a same peak value as the first waveform template.

16. The method according to claim 12 wherein the calculating of the qualities of at least some of the first cardiac cycle waveforms comprises calculating relationships between peaks of the at least some of the first cardiac cycle waveforms and a peak of the first waveform template.

17. A non-transitory computer readable medium that stores instructions that once executed by a computerized device cause the computerized device to execute the steps of:
receiving first and second detection signals and electrocardiograph signals;
wherein the first detection signals result from an illumination by infrared pulses of a sternal angle of a user, and being detected by an oxygen saturation sensor included in a device that is removably attached to a user;
wherein the second detection signals result from an illumination by visible light pulses detected by the oxygen saturation sensor, of the sternal angle of a user;
wherein the electrocardiograph signals are detected by an electrocardiography sensor that is included in the device;
generating a first waveform template that is responsive to the first detection signals;
generating a second waveform template that is responsive to the second detection signals;
calculating an indication of the oxygen saturation characteristic of the user in response to the first and second detection signals;
detecting cardiac cycle durations that are based upon the first and second detection signals;
detecting electrocardiography based cardiac cycle durations using an electrocardiography sensor; and
evaluating a quality of the indication of the oxygen saturation characteristic of the user by comparing the first waveform template, and the second waveform template to the cardiac cycle's durations and to the electrocardiography based cardiac cycle durations.

18. A medical device that comprises a processor that is configured to receive first and second detection signals and electrocardiograph signals and having an illumination source for generating infrared and visible light pulses and having an electrocardiograph sensor for detecting electrocardiography based cardiac cycle durations;
wherein the first detection signals result from an illumination by infrared pulses, by an oxygen saturation sensor included in the device which is removably attached to a user, of a sternal angle of a user;
wherein the second detection signals result from an illumination, by the oxygen saturation sensor, of the sternal angle of a user;
wherein the electrocardiograph signals may be detected by the electrocardiography sensor included in the device;
(ii) generate a first waveform template responsive to the first detection signals;
(iii) generate a second waveform template responsive to the second detection signals;
(iv) calculate an indication of the oxygen saturation characteristic of the user in response to the first and second detection signals;
(v) detect cardiac cycle durations based upon the first and second detection signals;
(vi) using the electrocardiography sensor detect electrocardiography based cardiac cycle durations; and
(vii) evaluate a quality of the indication of the oxygen saturation characteristic of the user in response to comparing the first waveform template, and the second waveform template to the cardiac cycle's durations and to the electrocardiography based cardiac cycle durations.

* * * * *